United States Patent
Schnermann et al.

(10) Patent No.: US 10,280,307 B2
(45) Date of Patent: May 7, 2019

(54) CLASS OF STABLE HEPTAMETHINE CYANINE FLUOROPHORES AND BIOMEDICAL APPLICATIONS THEREOF

(71) Applicant: THE UNITED STATES OF AMERICA, AS REPRESENTED BY THE SECRETARY, DEPARTMENT OF HEALTH AND HUMAN SERVICES, Washington, DC (US)

(72) Inventors: Martin John Schnermann, Rockville, MD (US); Roger Rauhauser Nani, Frederick, MD (US); James Blaine Shaum, Frederick, MD (US)

(73) Assignee: THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 51 days.

(21) Appl. No.: 15/524,567

(22) PCT Filed: Nov. 5, 2014

(86) PCT No.: PCT/US2014/064136
§ 371 (c)(1),
(2) Date: May 4, 2017

(87) PCT Pub. No.: WO2016/072984
PCT Pub. Date: May 12, 2016

(65) Prior Publication Data
US 2018/0273758 A1  Sep. 27, 2018

(51) Int. Cl.
*A61K 49/00* (2006.01)
*C09B 23/08* (2006.01)
*C07D 209/10* (2006.01)
*C07D 209/12* (2006.01)
*C07D 209/14* (2006.01)
*C09K 11/06* (2006.01)
*G01N 33/58* (2006.01)

(52) U.S. Cl.
CPC ........ *C09B 23/086* (2013.01); *A61K 49/0032* (2013.01); *C07D 209/10* (2013.01); *C07D 209/12* (2013.01); *C07D 209/14* (2013.01); *C09K 11/06* (2013.01); *G01N 33/582* (2013.01); *C09K 2211/1018* (2013.01)

(58) Field of Classification Search
CPC .................................................. A61K 49/00
See application file for complete search history.

(56) References Cited

U.S. PATENT DOCUMENTS 7,198,778 B2  4/2007  Achilefu et al.
8,344,158 B2  1/2013  Achilefu et al.
2004/0081622 A1  4/2004  Achilefu et al.
2004/0141920 A1  7/2004  Achilefu et al.
2008/0031823 A1  2/2008  Bornhop et al.
2014/0271476 A1*  9/2014  Kularatne .......... A61K 49/0052
424/9.1

FOREIGN PATENT DOCUMENTS

JP      2011-051961 A    3/2011
WO   WO 2007/005222 A2   1/2007
WO   WO 2011/119114 A1   9/2011
WO   WO 2013/036543 A2   3/2013
WO   WO 2014/149069 A1   9/2014

OTHER PUBLICATIONS

Biswas et al. "Biomolecular robotics for chemomechanically driven guest delivery fuelled by intracellular ATP." *Nature Chemistry* 5: 613-620 (2013).
Bouteiller et al. "Novel water-soluble near-infrared cyanine dyes: synthesis, spectral properties, and use in the preparation of internally quenched fluorescent probes." *Bioconjugate Chemistry* 18: 1303-1317 (2007).
Gorka et al., "A near-IR uncaging strategy based on cyanine photochemistry," *Journal of the American Chemical Society* 136: 14153 (2014), dx.doi.org/10.1021/ja5065203.
Hilderbrand et al., "Monofunctional near-infrared fluorochromes for imaging applications," *Bioconjugate Chemistry* 16: 1275-1281 (2005).
International Search Report and Written Opinion of parent PCT/US2014/064136, dated Dec. 17, 2014 (9 pages).
Lim et al., "Tunable heptamethine-azo dye conjugate as an NIR fluorescent probe for the selective detection of mitochondrial glutathione over cysteine and homocysteine," *Journal of the American Chemical Society* 136: 7018-7025 (2014).
Nani, et al., "N- to O-Rearrangement of Cyanines: Synthesis of Stable NIR Fluorophores," *Chemical Biology Laboratory, National Cancer Institute*, 1 page (Sep. 24, 2014).
Narayanan et al., "A new method for the synthesis of heptamethine cyanine dyes: synthesis of new near-infrared fluorescent labels," *J. Org. Chem.* 60:2391-2395 (1995).

(Continued)

*Primary Examiner* — Michael G. Hartley
*Assistant Examiner* — Jagadishwar R Samala
(74) *Attorney, Agent, or Firm* — Klarquist Sparkman, LLP

(57) ABSTRACT

Embodiments of C4'-alkyl-ether heptamethine cyanine fluorophores according to general formula I, and pharmaceutically acceptable salts thereof, are disclosed. Methods of making and using the C4'-alkyl-ether heptamethine cyanine fluorophores also are disclosed.

(I)

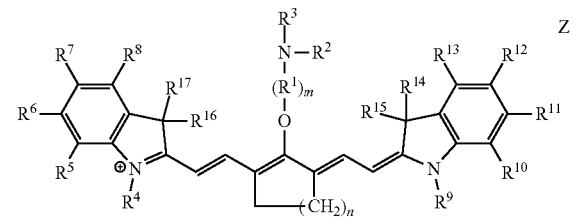

25 Claims, 10 Drawing Sheets

(56) References Cited

OTHER PUBLICATIONS

Pascal et al. "Expanding the polymethine paradigm: evidence for the contribution of a bis-dipolar electronic structure," *The Journal of Physical Chemistry A* 118: 4038-4047 (2014).
Peng et al., "Heptamethine cyanine dyes with a large stokes shift and strong fluorescence: a paradigm for excited-state intramolecular charge transfer," *Journal of the American Chemical Society* 127: 4170-4171 (2005).
Shealy et al., "Synthesis, chromatographic separation, and characterization of near-infrared-labeled DNA oligomers for use in DNA sequencing," *Anal. Chem.* 67:247-251 (1995).
Strekowski et al., "Water-soluble pH-sensitive 2, 6-bis (substituted ethylidene)-cyclohexanone/hydroxy cyanine dyes that absorb in the visible/near-infrared regions," *Journal of Heterocyclic Chemistry* 41: 227-232 (2004).
Zaheer et al., "IRDye78 conjugates for near-infrared fluorescence imaging," *Molecular Imaging* 1(4): 354-364 (2002).
Zhang et al., "Synthesis and evaluation of polyhydroxylated near-infrared carbocyanine molecular probes," *Org. Lett.* 6(12): 2067-2070 (2004).

* cited by examiner

FIG. 1J
FIG. 1I
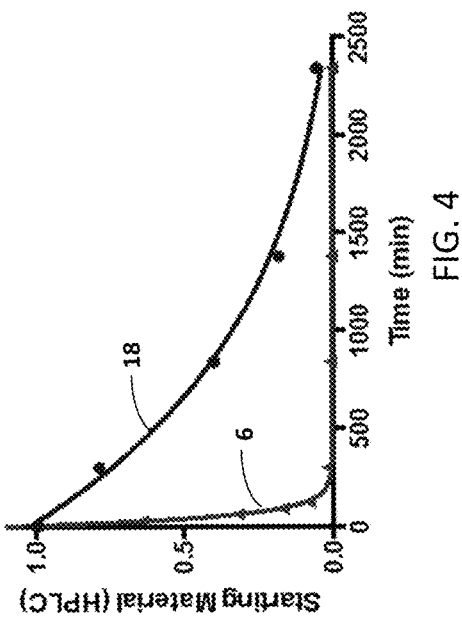
FIG. 4

FIG. 12A
FIG. 12B
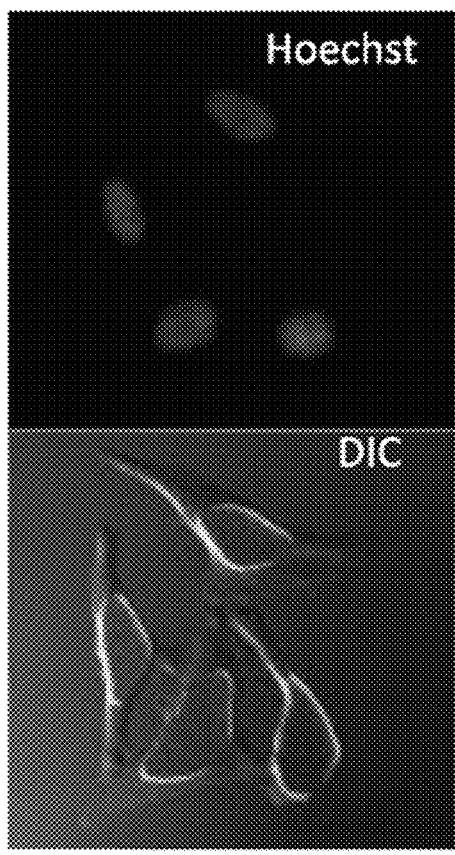
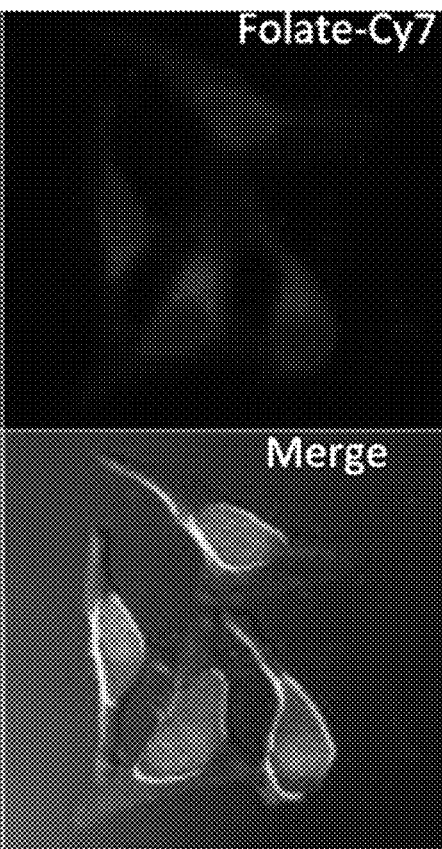
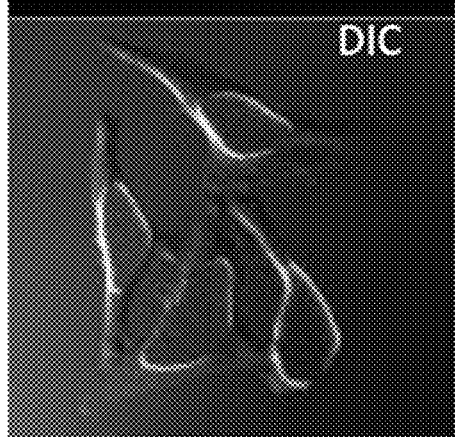
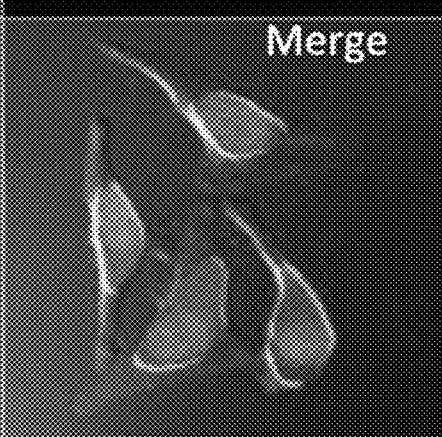
FIG. 12C
FIG. 12D

CLASS OF STABLE HEPTAMETHINE CYANINE FLUOROPHORES AND BIOMEDICAL APPLICATIONS THEREOF

CROSS REFERENCE TO RELATED APPLICATION

This is the U.S. National Stage of International Application No.PCT/US2014/064136, filed Nov. 5, 2014, which was published in English under PCT Article 21(2).

FIELD

This disclosure concerns heptamethine cyanine fluorophores, and methods of making and using the fluorophores.

BACKGROUND

Fluorescent small molecules are central in many modern biological techniques. Their preparation often relies on inefficient condensation reactions requiring harsh reaction conditions with poor substrate scope. Thus, there is a need for new methods to prepare fluorophores for modern applications.

Near-infrared (near-IR, 650-900 nm) fluorophores find increasing use for a variety of techniques due to the low autofluorescence in this range. Near-IR fluorophores are uniquely well suited for in vivo fluorescence imaging due to improved tissue penetration of near-IR compared to shorter wavelengths. Heptamethine cyanines, with emission maxima around 800 nm, are perhaps the archetype (Frangioni, *Curr. Opin. Chem. Biol.* 2003, 7, 626-634; Alford et al., *Molecular Imaging* 2009, 8, 341-354). While useful in a variety of applications, including for certain clinical diagnostic procedures, many suffer from chemical stability issues at C4' and challenging synthesis. Cyanines modified at the C4' position with an O-alkyl substituent are desirable because these are likely to be quite stable and there is potential for a concise route to symmetrical bioconjugatable variants. However, such molecules have only rarely been described and are unknown when functionalized for biomolecule conjugation. The scarcity of C4'-O-alkyl ether cyanines is based on the inability of most alkoxide nucleophiles to undergo the standard preparative reaction, C4'-chloride exchange (Strekowski et al., *J. Org. Chem.* 1992, 57, 4578-4580). This failure likely stems from the poor kinetics of alkoxides in the proposed electron transfer $S_{RN}1$ pathway, and competitive addition to the imine-like C2 position has been reported to intercede (Strekowski et al., *J. Org. Chem.* 1992, 57, 4578-4580; Strekowski et al., *Dyes Pigments* 2000, 46, 163-168). Thus, a need exists for stable, near-IR heptamethine cyanine fluorophores and a synthetic method for making the fluorophores.

SUMMARY

This disclosure concerns a synthetic method for making cyanine fluorophores, particularly stable heptamethine cyanine (Cy7) fluorophores, embodiments of Cy7 fluorophores made by the disclosed method and pharmaceutical salts thereof, and methods of using the Cy7 fluorophores.

Embodiments of the disclosed Cy7 fluorophores have a structure according to formula I

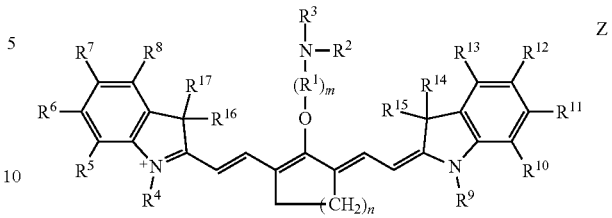

wherein m is 2, 3, 4, or 5; n is 1, 2, or 3; $R^1$ is $-CR^a{}_2-$ where each $R^a$ independently is H, halo, optionally substituted alkyl, or optionally substituted aryl; $R^2$ is optionally substituted alkyl, optionally substituted heteroalkyl, optionally substituted aryl, or optionally substituted heteroaryl; $R^3$ is a maleimidyl-containing group, a succinimidyl-containing group, optionally substituted alkoxy, optionally substituted alkyl carbonyl, optionally substituted alkoxy carbonyl, a drug, or a biomolecule-containing group; $R^4$ to $R^{13}$ independently are H, optionally substituted alkyl, optionally substituted amino, or a sulfonate-containing group, wherein $R^6$ and $R^7$ optionally together form a substituted or unsubstituted cycloalkyl or aryl, and $R^{12}$ and $R^{13}$ optionally together form a substituted or unsubstituted cycloalkyl or aryl; $R^{14}$ to $R^{17}$ independently are alkyl; and Z is a monatomic or polyatomic ion having a charge sufficient to provide a neutral compound.

In some embodiments, $R^3$ is a biomolecule-containing group. The biomolecule may be an antibody, a peptide, a protein, an amino acid, a nucleoside, a nucleotide, a nucleic acid, an oligonucleotide, a carbohydrate, a lipid, a hapten, or a receptor ligand.

In any or all of the above embodiments, $R^3$ may be

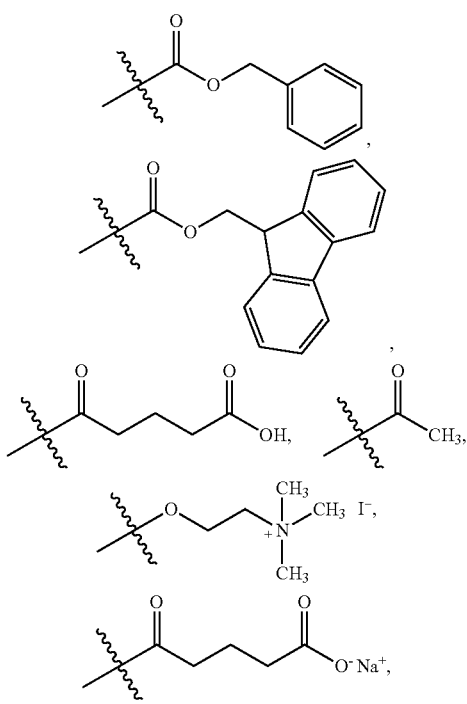

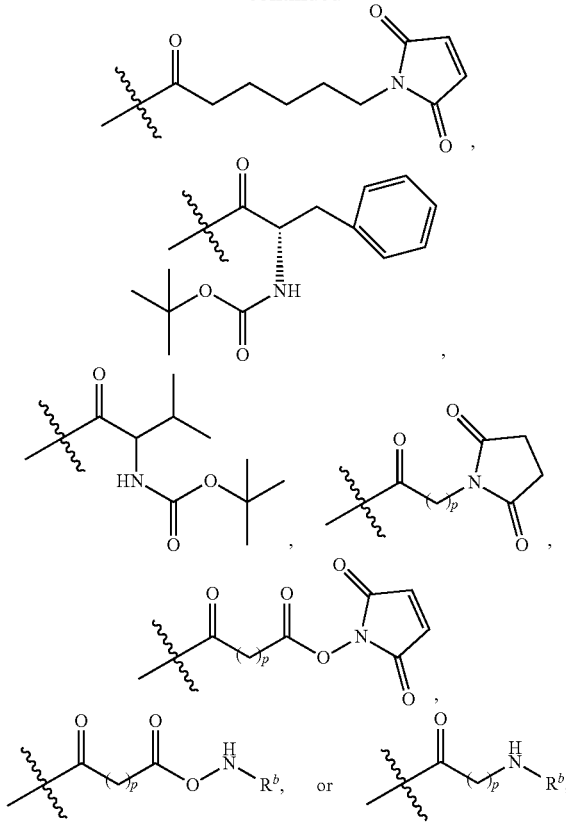

where p is 1, 2, 3, 4, or 5, and $R^b$ is a biomolecule. In some embodiments, $R^b$ is an antibody, a peptide, a protein, an amino acid, a nucleic acid, nucleotide, an oligonucleotide, a lipid, a hapten, or a receptor ligand.

In any or all of the above embodiments, each $R^a$ independently may be hydrogen or halo, and m is 2 or 3. In any or all of the above embodiments, $R^{14}$ to $R^{17}$ may be methyl. In any or all of the above embodiments, n may be 2.

In any or all of the above embodiments, $R^5$, $R^6$, $R^8$, $R^{10}$, $R^{11}$ and $R^{13}$ may be hydrogen; $R^4$ and $R^9$ independently may be lower alkyl or a sulfonate-containing group; and $R^7$ and $R^{12}$ independently may be hydrogen, a sulfonate-containing group, or a trialkyl amino group. In some embodiments, $R^4$ and $R^9$ are n-propyl or —$(CH_2)_4SO_3^-$; and $R^7$ and $R^{12}$ are hydrogen or —$SO_3^-Na^+$.

In an independent embodiment, a Cy7 fluorophore has the general formula

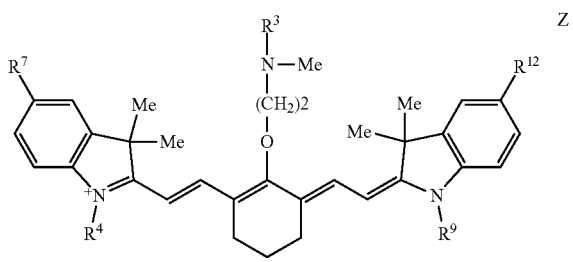

where $R^3$, $R^4$, $R^7$, $R^9$, and $R^{12}$ are as defined above.

In an independent embodiment, n is 2; $R^1$ is —$CH_2$—; m is 2; $R^2$ and $R^{14}$ to $R^{17}$ are methyl; $R^5$, $R^6$-$R^8$ and $R^{11}$-$R^{13}$ are hydrogen; $R^4$ and $R^9$ are n-propyl; Z is halide, and $R^3$ is

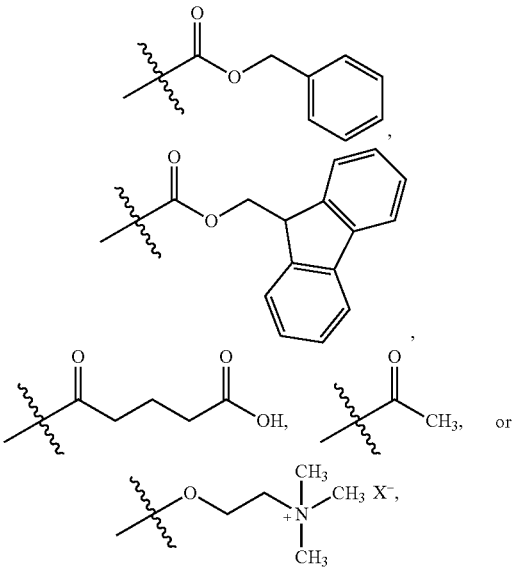

where $X^-$ is a halide.

In an independent embodiment, n is 2; $R^1$ is —$CH_2$—; m is 2; $R^2$ and $R^{14}$ to $R^{17}$ are methyl; $R^5$, $R^6$, $R^8$, $R^{10}$, $R^{11}$ and $R^{13}$ are hydrogen; $R^4$ and $R^9$ are —$(CH_2)_4SO_3^-$; $R^7$ and $R^{12}$ are —$SO_3^-$; Z is an alkali metal cation, and $R^3$ is

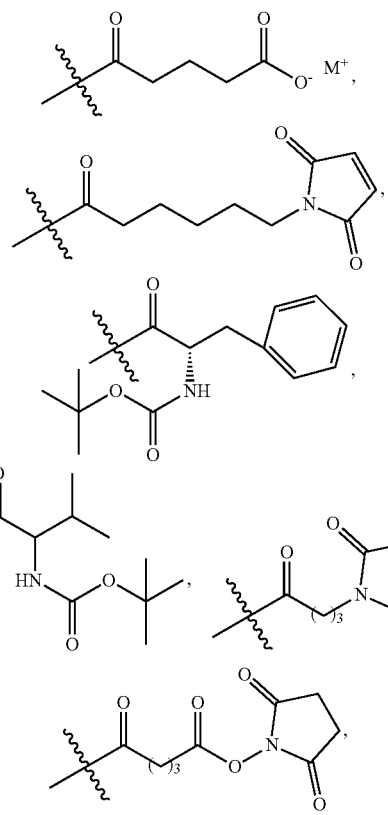

where $M^+$ is a proton or an alkali metal cation.

A method of making the disclosed Cy7 fluorophores includes providing a first solution comprising a solvent and an ionic precursor of formula (i)

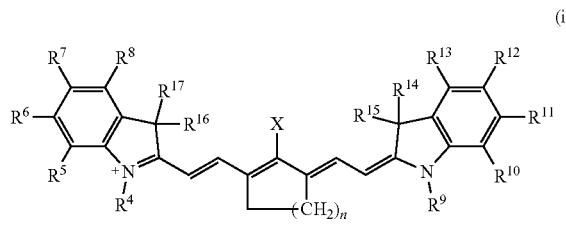

(i)

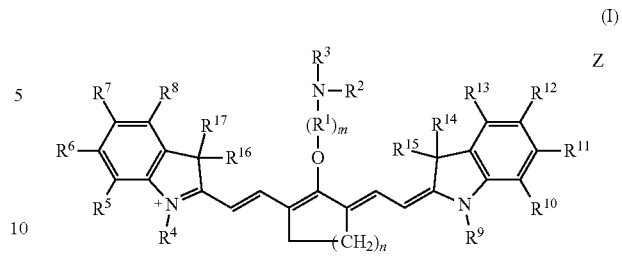

(I)

wherein n is 1, 2, or 3, $R^4$ to $R^{13}$ independently are H; optionally substituted alkyl; optionally substituted amino; or a sulfonate-containing group, wherein $R^6$ and $R^7$ optionally together form a substituted or unsubstituted cycloalkyl or aryl, and $R^{12}$ and $R^{13}$ optionally together form a substituted or unsubstituted cycloalkyl or aryl, $R^{14}$ to $R^{17}$ independently are alkyl, and X is halo. $R^2(H)N-(R^1)_m-OH$ is added to the first solution, wherein $R^1$ is $-CR^a{}_2-$ where each $R^a$ independently is H, halo, optionally substituted alkyl, or optionally substituted aryl; m is 2, 3, 4, or 5; and $R^2$ is optionally substituted alkyl, optionally substituted heteroalkyl, optionally substituted aryl, or optionally substituted heteroaryl, and the first solution is heated at an effective temperature for an effective period of time to form a solution comprising an ion according to formula (ii).

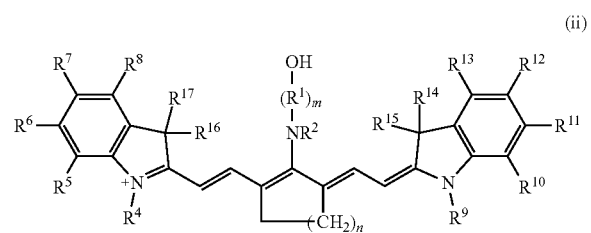

(ii)

A salt comprising the ion according to formula (ii) is recovered. A second solution is formed, wherein the second solution comprises a solvent, the salt, and a compound comprising $R^3$, wherein $R^3$ is a maleimidyl-containing group, a succinimidyl-containing group, optionally substituted alkoxy, optionally substituted alkyl carbonyl, optionally substituted alkoxy carbonyl, a biomolecule-containing group, or a combination thereof. In some embodiments, the second solution further comprises a base. The second solution is reacted under conditions effective to form an ion according to formula (iii).

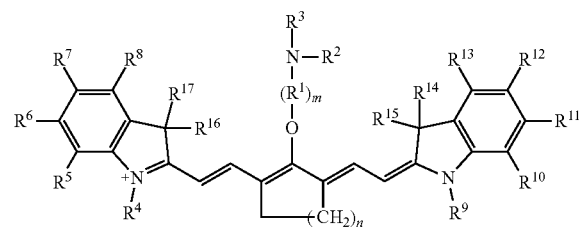

(iii)

A compound according to formula I is recovered, wherein Z is a monatomic or polyatomic ion having a charge sufficient to provide a neutral compound.

In any or all of the above embodiments, the compound comprising $R^3$ may be combined with N-[(dimethylamino)-1H-1,2,3-triazolo-[4,5-b]pyridin-1-ylmethylene]-N-methyl-methanaminium hexafluorophosphate N-oxide and diisopropylethylamine before forming the second solution.

In any or all of the above embodiments, when $R^3$ terminates in a succinimidyl moiety, a maleimidyl moiety, $-COOH$, or $-COO^-$, the method may further include reacting the compound according to formula I with a biomolecule under effective conditions to form a fluorophore-biomolecule conjugate.

A method for using embodiments of the disclosed Cy7 fluorophores includes contacting a biological sample with a Cy7 fluorophore as disclosed herein, irradiating the biological sample by application of light having a wavelength or range of wavelengths in the near-infrared range, and detecting fluorescence of the irradiated biological sample, wherein fluorescence indicates presence of the Cy7 fluorophore in the biological sample.

Detecting fluorescence may comprise obtaining a fluorescence-based image of the irradiated biological sample. In an independent embodiment, the Cy7 fluorophore comprises a biomolecule capable of binding to a target suspected of being present within the biological sample, fluorescence indicates the target is present in the biological sample, and the method further includes removing unbound compound from the biological sample prior to obtaining the image.

In an independent embodiment, the biological sample comprises cells in solution, the Cy7 fluorophore comprises a moiety capable of binding to at least some cells in the solution, and the method further includes performing flow cytometry to separate cells to which the compound has bound from cells to which the compound did not bind.

In any or all of the above embodiments, contacting the biological sample with the Cy7 fluorophore may be performed in vivo by administering the compound to a subject. In any or all of the above embodiments, detecting fluorescence of the biological sample may be performed ex vivo.

In some embodiments, a Cy7 fluorophore administered in vivo includes a biomolecule capable of binding to a target suspected of being present within the biological sample. In one embodiment, irradiating the biological sample comprises irradiating a target area of the subject with near-infrared radiation, and detecting fluorescence comprises obtaining an image of the irradiated target area, wherein fluorescence in the image indicates presence of the target in the target area. In an independent embodiment, the target is an antigen, and the Cy7 fluorophore comprises an antibody capable of recognizing and binding to the antigen. In another independent embodiment, the Cy7 fluorophore comprises a drug, the biological sample is a bodily fluid or tissue, and detecting fluorescence of the irradiated biological sample indicates presence of the drug in the biological sample. In some embodiments, the biological sample is a tumor and the target area is an area in which the tumor is located. In such embodiments, the biomolecule may be capable of recognizing and binding to cells of the tumor, irradiating the biological sample may comprise irradiating the target area of the subject with near-infrared radiation, detecting fluorescence may indicate presence of tumor cells in the target area, and the method may further include excising fluorescent tumor cells from the target area.

The foregoing and other objects, features, and advantages of the invention will become more apparent from the following detailed description, which proceeds with reference to the accompanying figures.

BRIEF DESCRIPTION OF THE DRAWINGS

FIGS. 1A-1J are absorbance spectra of exemplary C4'-alkyl-ether heptamethine cyanine fluorophores.

FIG. 4 is a graph of starting material versus time, showing kinetic differences in rearrangement of two alkanolamine-substituted compounds to form exemplary C4'-alkyl-ether heptamethine cyanine fluorophores.

FIGS. 12A-12D are microscopy images of HeLa cells conditioned to overexpress the folate receptor. FIG. 12A is a fluorescence image of the cells stained with Hoechst 33342. FIG. 12B is a fluorescence image of the cells incubated with a conjugate of folate and an exemplary C4'-alkyl-ether heptamethine cyanine fluorophore (Folate-Cy7). FIG. 12C is a differential interference contrast (DIC) image of the cells. FIG. 12D is a merged image of the images in FIGS. 12B and 12C.

DETAILED DESCRIPTION

Figure 1A:
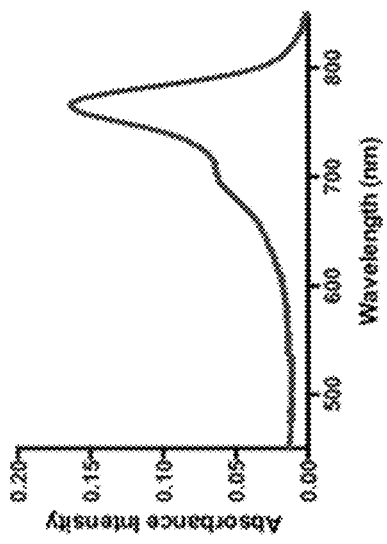

This disclosure concerns a synthetic method for making cyanine fluorophores, particularly stable heptamethine cyanine (Cy7) fluorophores, embodiments of Cy7 fluorophores made by the disclosed method, and methods of using the Cy7 fluorophores. The disclosed Cy7 fluorophores are C4'-O-alkyl heptamethine cyanines demonstrating optical properties that are ideal for near-IR imaging applications and excellent resistance to thiol nucleophiles. Some embodiments of the disclosed Cy7 fluorophores are suitable for bioconjugation.

I. Definitions

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the disclosure, the following explanations of specific terms are provided:

Alkoxy: A group having the structure —OR, where R is a substituted or unsubstituted alkyl. Methoxy (—OCH$_3$) is an exemplary alkoxy group. In a substituted alkoxy, R is alkyl substituted with a non-interfering substituent.

Alkoxy carbonyl: A group having the structure —(O)C—O—R, where R is a substituted or unsubstituted alkyl.

Alkyl: A hydrocarbon group having a saturated carbon chain. The chain may be branched, unbranched, or cyclic (cycloalkyl). The term lower alkyl means the chain includes 1-10 carbon atoms. Unless otherwise specified, the term alkyl encompasses substituted and unsubstituted alkyl.

Alkyl carbonyl: A group having the structure —(O)C—R, where R is a substituted or unsubstituted alkyl.

Amino: A group having the structure —N(R)R' where R and R' are independently hydrogen, alkyl, heteroalkyl, haloalkyl, aliphatic, heteroaliphatic, aryl (such as optionally substituted phenyl or benzyl), heteroaryl, alkylsulfano, or other functionality. A "primary amino" group is —NH$_2$. "Mono-substituted amino" means a radical —N(H)R substituted as above and includes, e.g., methylamino, (1-methylethyl)amino, phenylamino, and the like. "Di-substituted amino" means a radical —N(R)R' substituted as above and includes, e.g., dimethylamino, methylethylamino, di(1-methylethyl)amino, and the like. The term amino also encompasses charged tri-substituted amino groups, e.g., —N(R)(R')R"+ where R, R', and R" are independently hydrogen, alkyl, heteroalkyl, haloalkyl, aliphatic, heteroaliphatic, aryl (such as optionally substituted phenyl or benzyl), heteroaryl, alkylsulfano, or other functionality.

Aryl: A monovalent aromatic carbocyclic group of, unless specified otherwise, from 6 to 15 carbon atoms having a single ring (e.g., phenyl) or multiple condensed rings in which at least one ring is aromatic (e.g., quinoline, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic. Unless otherwise specified, the term aryl encompasses substituted and unsubstituted aryl.

Bioconjugate: Two or more moieties directly or indirectly coupled together, where one of the moieties is a biomolecule. For example, a first moiety may be covalently or noncovalently (e.g., electrostatically) coupled to a second moiety. Indirect attachment is possible, such as by using a "linker" (a molecule or group of atoms positioned between two moieties).

Biomolecule: Any molecule that may be included in a biological system, including but not limited to, a synthetic or naturally occurring antibody, protein (including glycoproteins and lipoproteins), amino acid, nucleoside, nucleotide, nucleic acid, oligonucleotide, DNA, RNA, carbohydrate (including monosaccharides, disaccharides, oligosaccharides, and polysaccharides), lipid (including fatty acids, monoglycerides, diglycerides, triglycerides, sterols, phospholipids, and fat-soluble vitamins), hapten, a receptor ligand (i.e., a moiety that binds to a cellular receptor), and the like.

Cy7: The abbreviation "Cy7" refers to heptamethine cyanine.

Halogen: The terms halogen and halo refer to fluorine, chlorine, bromine, iodine, and radicals thereof.

Heteroalkyl: An alkyl group as defined above containing at least one heteroatom, such as N, O, S, or S(O)$_n$ (where n is 1 or 2). Unless otherwise specified, the term heteroalkyl encompasses substituted and unsubstituted heteroalkyl.

Heteroaryl: An aromatic compound or group having at least one heteroatom, i.e., one or more carbon atoms in the ring has been replaced with an atom having at least one lone pair of electrons, typically nitrogen, oxygen, phosphorus, silicon, or sulfur. Unless otherwise specified, the term heteroaryl encompasses substituted and unsubstituted heteroaryl.

Maleimidyl-containing group: The term maleimidyl-containing group includes

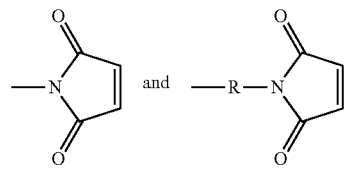

groups, where R is substituted or unsubstituted alkyl, substituted or unsubstituted heteroalkyl, substituted or unsubstituted aryl, or substituted or unsubstituted heteroaryl.

Near-infrared (near-IR, NIR): Wavelengths within the range of 650-900 nm.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more C4'-alkyl-ether heptamethine cyanine fluorophores as disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutically acceptable salt: A biologically compatible salt of a compound that can be used as a drug, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19, which is incorporated herein by reference.)

Stokes shift: The difference (in wavelength or frequency units) between absorbance spectrum maximum and the emission spectrum maximum of the same electronic transition. Typically, the wavelength of maximum fluorescence emission is longer than that of the exciting radiation, i.e., the wavelength of maximum absorbance.

Substituent: An atom or group of atoms that replaces another atom in a molecule as the result of a reaction. The term "substituent" typically refers to an atom or group of atoms that replaces a hydrogen atom, or two hydrogen atoms if the substituent is attached via a double bond, on a parent hydrocarbon chain or ring. The term "substituent" may also cover groups of atoms having multiple points of attachment to the molecule, e.g., the substituent replaces two or more hydrogen atoms on a parent hydrocarbon chain or ring. In such instances, the substituent, unless otherwise specified, may be attached in any spatial orientation to the parent hydrocarbon chain or ring. Exemplary substituents include, for instance, alkyl, alkenyl, alkynyl, alkoxy, alkylamino, alkylthio, acyl, aldehyde, amido, amino, aminoalkyl, aryl, arylalkyl, arylamino, carbonate, carboxyl, cyano, cycloalkyl, dialkylamino, halo, haloaliphatic (e.g., haloalkyl), haloalkoxy, heteroaliphatic, heteroaryl, heterocycloaliphatic, hydroxyl, isocyano, isothiocyano, oxo, sulfonamide, sulfhydryl, thio, and thioalkoxy groups.

Substituted: A fundamental compound, such as an aryl or aliphatic compound, or a radical thereof, having coupled thereto one or more substituents, each substituent typically replacing a hydrogen atom on the fundamental compound. Solely by way of example and without limitation, a substituted aryl compound may have an aliphatic group coupled to the closed ring of the aryl base, such as with toluene. Again solely by way of example and without limitation, a long-chain hydrocarbon may have a hydroxyl group bonded thereto.

Succinimidyl-containing group: The term succinimidyl-containing group includes

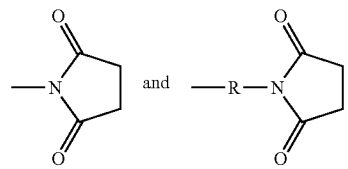

groups, where R is substituted or unsubstituted alkyl, substituted or unsubstituted heteroalkyl, substituted or unsubstituted aryl, or substituted or unsubstituted heteroaryl.

Sulfonate-containing group: A group including $SO_3^-$. The term sulfonate-containing group includes —$SO_3^-$ and —$RSO_3^-$ groups, where R is substituted or unsubstituted alkyl, substituted or unsubstituted heteroalkyl, substituted or unsubstituted aryl, or substituted or unsubstituted heteroaryl.

Target: A molecule for which the presence, location and/or concentration is to be determined. Examples of targets include proteins and nucleic acid sequences present in tissue samples. A target area is an area in which a target molecule is located or potentially located.

II. Synthesis Of C4'-Alkyl-Ether Heptamethine Cyanines

A synthetic method for making near-IR C4'-alkyl-ether heptamethine cyanine (Cy7) fluorophores involves nitrogen quaternization by electrophiles to initiate N- to O-transposition in a precursor compound (Scheme 1). With reference to Scheme 1, R is alkyl, heteroalkyl, aryl, or heteroaryl, Y is hydroxyl, E is an electrophile, and B is a base.

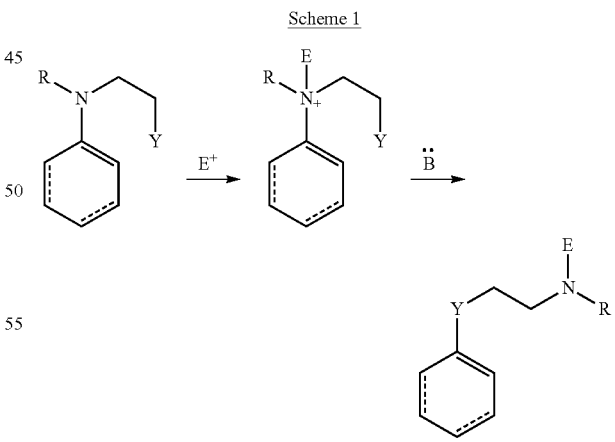

Scheme 1

An exemplary mechanism of the above process as applied to synthesis of C4'-alkyl-ether Cy7 fluorophores is shown in Scheme 2, wherein R is optionally substituted alkyl, optionally substituted heteroalkyl, optionally substituted aryl, or optionally substituted heteroaryl; E is an electrophile; and B is a base.

Scheme 2

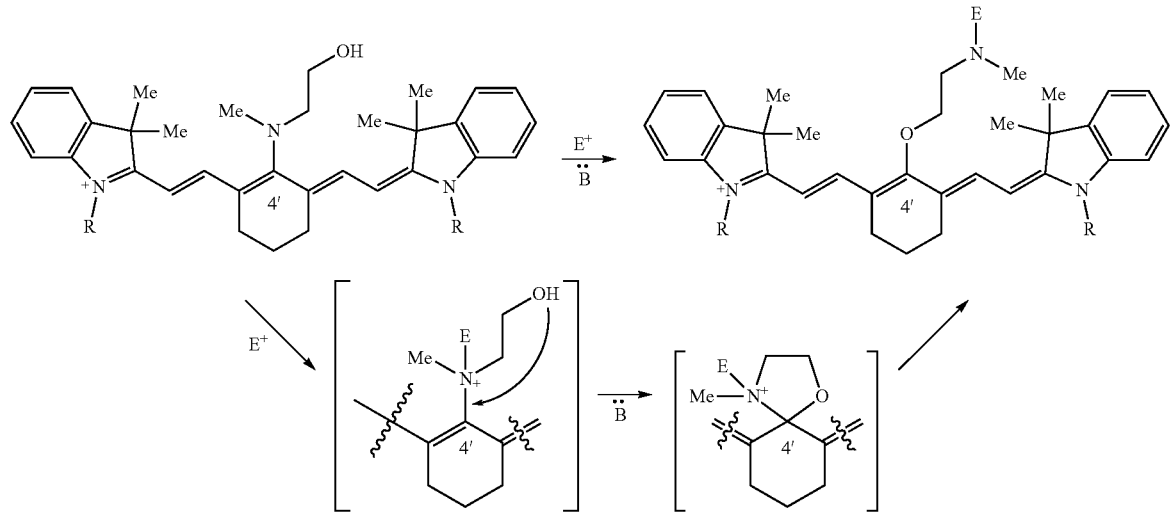

In general, embodiments of the disclosed C4'-alkyl-ether Cy7 fluorophores are synthesized from a halogenated precursor salt. In a first step (Scheme 3), an ionic halogenated precursor according to formula (i) is reacted with an alkanolamine to produce an alkanolamine-substituted precursor according to formula (ii).

fonate-bearing substituent at one or more of $R^4$, $R^7$, $R^9$, and $R^{12}$ may increase the compound's aqueous solubility and/or reduce aggregation—desirable traits for biological imaging. In an independent embodiment, $R^4$ and $R^9$ independently are lower alkyl or a sulfonate-containing group. In an independent embodiment, $R^4$ and $R^9$ are the same. In some Scheme 3

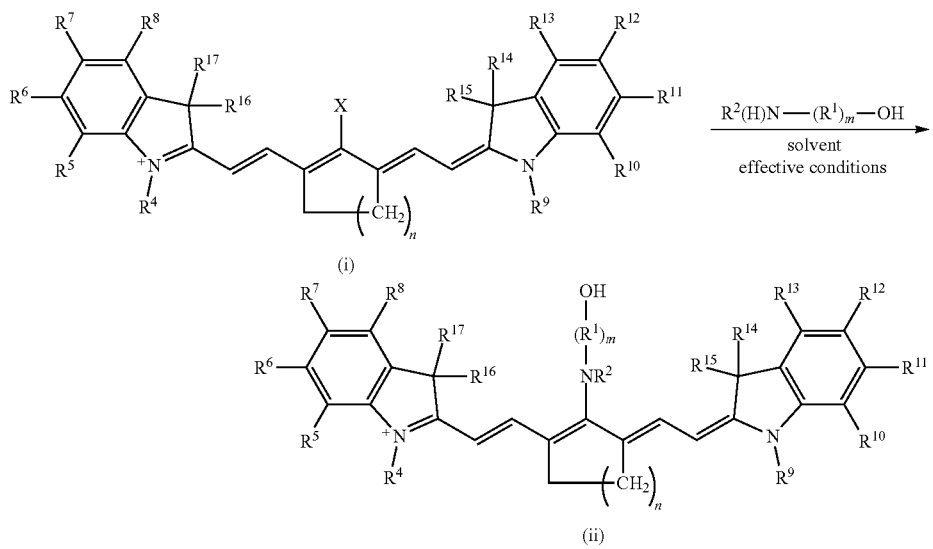

With respect to formulas (i) and (ii), n is 1, 2, or 3. $R^4$ to $R^{13}$ independently are H; optionally substituted alkyl; optionally substituted amino; or a sulfonate-containing group, wherein $R^6$ and $R^7$ optionally together form a substituted or unsubstituted cycloalkyl or aryl, and $R^{12}$ and $R^{13}$ optionally together form a substituted or unsubstituted cycloalkyl or aryl. $R^{14}$ to $R^{17}$ independently are alkyl. X is halo.

$R^4$ to $R^{13}$ are selected to provide desired properties of the final compound, such as solubility and/or cell permeability. In some embodiments, $R^4$, $R^7$, $R^9$, and $R^{12}$ may be selected to provide the desired characteristics. For example, a sulexamples, $R^4$ and $R^9$ are the same and are n-propyl or n-butylsulfonate (—$(CH_2)_4SO_3^-$). In an independent embodiment, $R^7$ and $R^{12}$ independently are hydrogen, a sulfonate-containing group, or a trialkyl amino group. In an independent embodiment, $R^7$ and $R^{12}$ are the same. In some examples, $R^7$ and $R^{12}$ are the same and are hydrogen or —$SO_3^-$ (e.g., —$SO_3^-Na^+$). In an independent embodiment, $R^5$, $R^6$, $R^8$, $R^{10}$, $R^{11}$ and $R^{13}$ are hydrogen.

In an independent embodiment, $R^{14}$ to $R^{17}$ independently are lower alkyl. In some examples, $R^{14}$ to $R^{17}$ are methyl. In some examples, X is chloro.

A first solution comprising an ionic precursor according to formula (i) is formed and an alkanolamine having the formula $R^2(H)N-(R^1)_m-OH$ is added to the first solution. $R^1$ is $-CR^a_2-$ where each $R^a$ independently is H, halogen, optionally substituted alkyl, or optionally substituted aryl, and m is 2, 3, 4, or 5. $R^2$ is optionally substituted alkyl, optionally substituted heteroalkyl, optionally substituted aryl, or optionally substituted heteroaryl.

In an independent embodiment, each $R^a$ is hydrogen and m is 2 or 3. In some examples, m is 2. In an independent embodiment, $R^2$ is alkyl, such as lower alkyl. In some examples, $R^2$ is methyl. In some examples, the alkanolamine is N-methylethanolamine. The solvent is any solvent or mixture of solvents capable of forming a solution or suspension of precursor (i) and the alkanolamine. In some embodiments, the solvent comprises acetonitrile or dimethylformamide.

A reaction between precursor (i) and the alkanolamine proceeds under effective conditions to form an alkanolamine-substituted precursor according to formula (ii). In some examples, the solution is placed in a sealed vial and heated at a temperature from 50-80° C. until a change in color has occurred, indicating that the reaction is complete. The reaction can be monitored by other means, e.g., liquid chromatography/mass spectroscopy (LC/MS). The solution may be heated from several minutes to several hours, such as from 45 minutes to two hours. Thus, in some embodiments, an effective temperature for the reaction is from 50-80° C., such as from 60-70° C., and an effective period of time is from 15 minutes to five hours, such as from 45 minutes to two hours. A salt of the alkanolamine-substituted precursor according to formula (ii) is recovered from the solution by any suitable means including, but not limited to, precipitation, ion exchange, chromatography (e.g., silica gel chromatography or liquid chromatography, including HPLC), or combinations thereof. In some examples, alkanolamine-substituted precursors according to formula (ii) exhibit a broad hypsochromic (blue-shifted) absorbance with maxima in the range of 640-700 nm, characteristic of a C4'-N-linkage.

Subsequently, an electrophile is reacted with the alkanolamine-substituted precursor according to formula (ii) to form a C4'-alkyl-ether heptamethine cyanine ion according to formula (iii) (Scheme 4).

Scheme 4

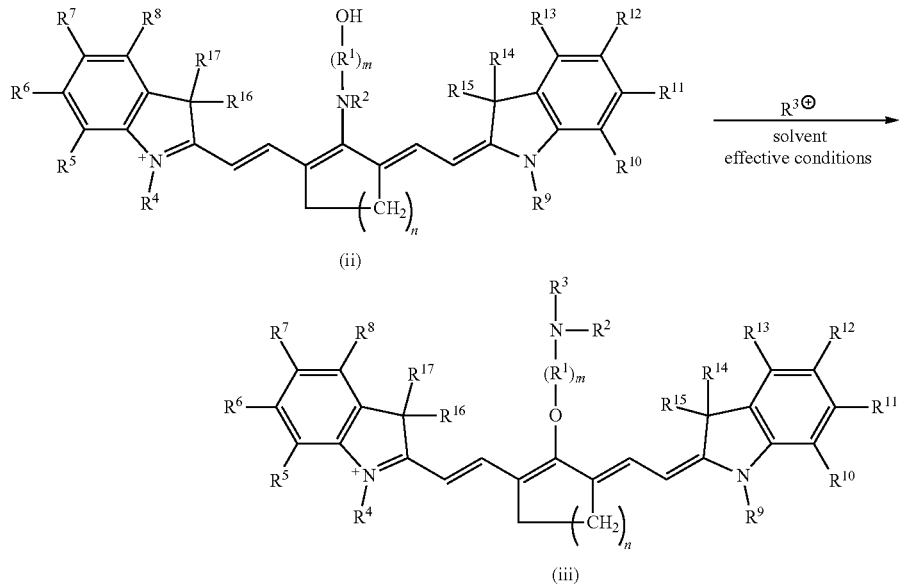

With respect to Scheme 4, $R^3$ is an electrophile capable of initiating an N- to O-rearrangement in the precursor according to formula (ii). In some embodiments, $R^3$ is a maleimidyl-containing group, a succinimidyl-containing group, optionally substituted alkoxy, optionally substituted alkyl carbonyl, optionally substituted alkoxy carbonyl, a biomolecule-containing group, or a combination thereof. Exemplary maleimidyl- and succinimidyl-containing groups may further include a carbonyl, alkyl carbonyl, alkoxy, or alkoxy carbonyl group attached to the ring nitrogen. In some embodiments, $R^3$ is formed by a combination of two groups that participate in the rearrangement, e.g., glutaric anhydride and N-hydroxysuccinimide may combine to form the succinimidyl-containing group $-(O)C(CH_2)_3C(O)O-NC_4H_4O_2$.

A solution comprising a solvent, a base, and the salt of the precursor according to formula (ii) and a compound comprising $R^3$ is formed. Suitable solvents include solvents in which the salt of precursor (ii) and the compound comprising $R^3$ can be dissolved or suspended.

Exemplary solvents include, but are not limited to, tetrahydrofuran (THF), N,N-dimethylformamide (DMF), dichloromethane (DCM), water, and combinations thereof.

Suitable bases include inorganic and organic bases. Exemplary bases include, but are not limited to, carbonates (e.g., $K_2CO_3$, $Na_2CO_3$), hydrogen carbonates (e.g., $KHCO_3$, $NaHCO_3$), hydroxides (e.g., KOH, NaOH), and organic amines (e.g., 4-dimethylaminopyridine (DMAP), N,N-diisopropylethylamine (DIPEA), 1-ethyl-3-(3-dimethylaminopropyl)carbodiimide (EDC, EDAC, or EDCI), and N-[(dimethylamino)-1H-1,2,3-triazolo-[4,5-b]pyridin-1-ylmethylene]-N-methylmethanaminium hexafluorophosphate N-oxide (HATU)).

Exemplary compounds comprising $R^3$ include, but are not limited to chloroformates, cyclic anhydrides, alkyl halides, carboxylic acids, and tetrafluoroborates. In some embodiments, the carboxylic acids are activated carboxylic acids, such as carboxylic acids preactivated with HATU and DIPEA before addition to the solution comprising precursor (ii).

A reaction of precursor (ii) and the compound comprising $R^3$ proceeds under effective conditions to form a C4'-alkyl-ether heptamethine cyanine ion according to formula (iii). Effective conditions may include reacting at a temperature ranging from room temperature (20-26° C.) to 100° C. for a time ranging from a few minutes to several hours. In the examples disclosed herein, the temperature ranged from room temperature to 90° C., and the time ranged from 10 minutes to 18 hours. In one example, the solution was irradiated with microwave irradiation at 90° C. In various embodiments, the solution is stirred gently, stirred vigorously, or not stirred. The reaction may proceed in a sealed vessel under an inert atmosphere (e.g., argon, nitrogen). Completion of the reaction may be monitored by any suitable means including, but not limited to, a visual color change or LC/MS.

A salt comprising the C4'-alkyl-ether heptamethine cyanine ion according to formula (iii) is recovered as a C4'-alkyl-ether Cy7 compound according to formula I, wherein Z is a monatomic or polyatomic ion having a charge sufficient to provide a neutral compound.

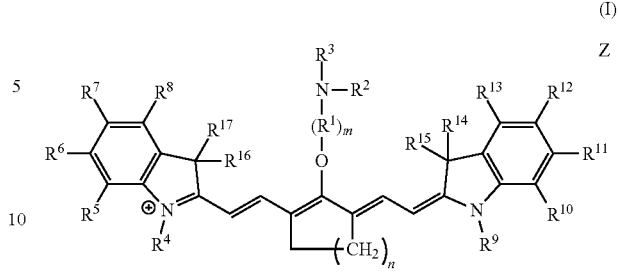

(I)

The compound according to formula I is recovered, and optionally purified, by suitable means. In some embodiments, the compound is recovered and/or purified by extraction, precipitation, evaporation, ion exchange, chromatography (e.g., silica gel chromatography, HPLC), and combinations thereof. Some compounds according to formula I exhibit a dramatic color change (blue to green) and a bathochromic-shifted (red-shifted) $\lambda_{max}$ relative to precursor (ii), indicative of the C4'-O-linkage.

Some embodiments of the disclosed compounds are suitable for further conjugation to a biomolecule. For example, when $R^3$ terminates in a succinimidyl moiety, a maleimidyl moiety, —COOH, or —COO$^-$, a biomolecule may be conjugated to the Cy7 fluorophore. Suitable biomolecules include, but are not limited to, antibodies, peptides, amino acids, proteins, and haptens. One exemplary bioconjugation reaction mediated by N,N'-disuccinimidyl carbonate is shown below in Scheme 5.

Scheme 5

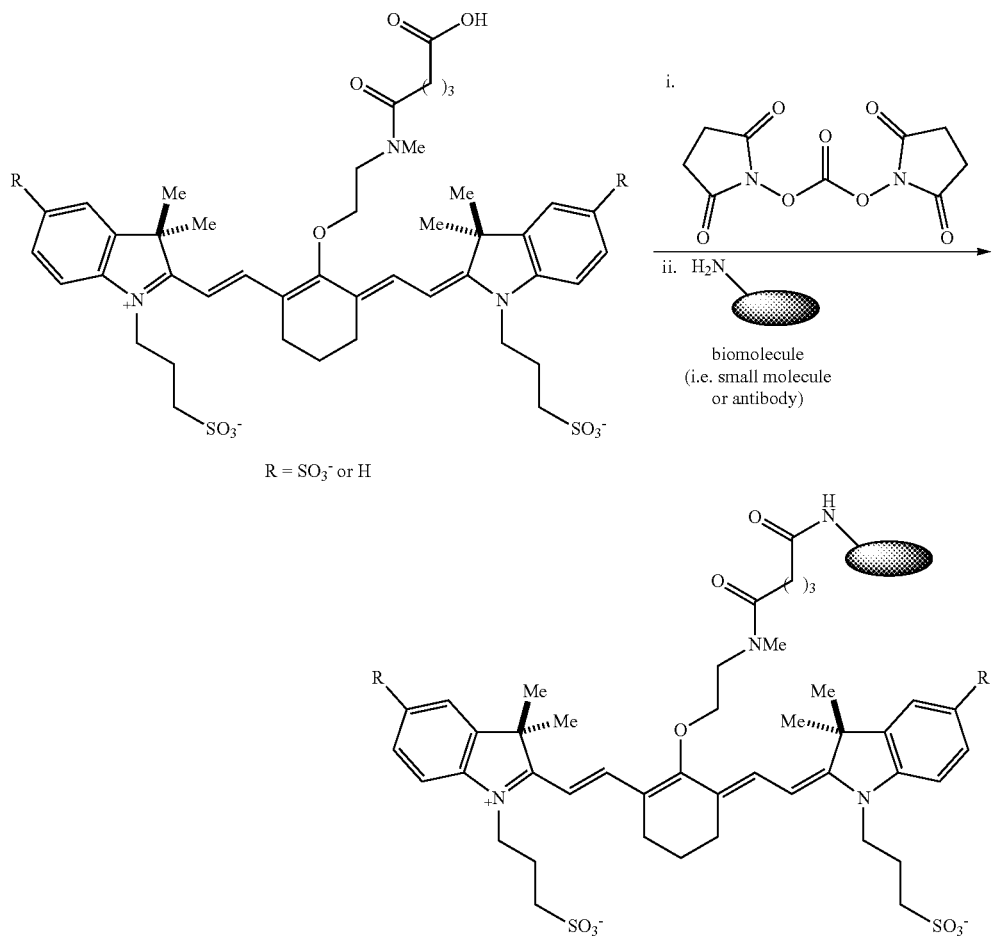

III. C4'-Alkyl-Ether Heptamethine Cyanine Fluorophores

Embodiments of C4'-alkyl-ether heptamethine cyanine fluorophores according to general formula I, and pharmaceutically acceptable salts thereof, are disclosed.

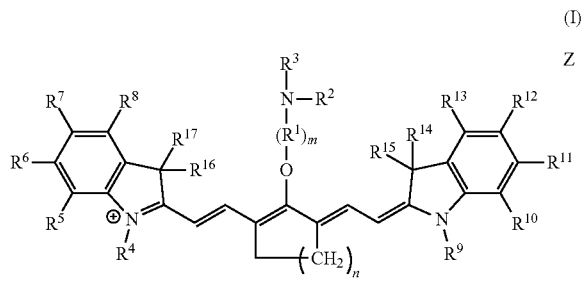

(I)

With respect to formula I, m is 2, 3, 4, or 5; n is 1, 2, or 3; $R^1$ is —$CR^a{}_2$— where each $R^a$ independently is H, halo, alkyl, or aryl; $R^2$ is optionally substituted alkyl, optionally substituted heteroalkyl, optionally substituted aryl, or optionally substituted heteroaryl; $R^4$ to $R^{13}$ independently are H, optionally substituted alkyl, optionally substituted amino, or a sulfonate-containing group, wherein $R^6$ and $R^7$ optionally together form a substituted or unsubstituted cycloalkyl or aryl, and $R^{12}$ and $R^{13}$ optionally together form a substituted or unsubstituted cycloalkyl or aryl; $R^{14}$ to $R^{17}$ independently are alkyl; and Z is a monatomic or polyatomic ion having a charge sufficient to provide a neutral compound. $R^3$ is an electrophile. In some embodiments, $R^3$ is a maleimidyl-containing group, a succinimidyl-containing group, optionally substituted alkoxy, optionally substituted alkyl carbonyl, optionally substituted alkoxy carbonyl, a drug, or a biomolecule-containing group. Exemplary biomolecules include, but are not limited to, antibodies, peptides, proteins, amino acids, nucleosides, nucleotides, nucleic acids, oligonucleotides, carbohydrates, lipids, haptens, and receptor ligands.

In an independent embodiment, each $R^a$ is hydrogen or fluoro and m is 2 or 3. In some examples, m is 2. In another independent embodiment, n is 2. In yet another independent embodiment, $R^2$ is alkyl, such as lower alkyl. In some examples, $R^2$ is methyl. In an independent embodiment, $R^{14}$ to $R^{17}$ independently are lower alkyl. In some examples, $R^{14}$ to $R^{17}$ are methyl. In an independent embodiment, $R^4$ and $R^9$ independently are lower alkyl or a sulfonate-containing group. In another independent embodiment, $R^4$ and $R^9$ are the same. In some examples, $R^4$ and $R^9$ are the same and are n-propyl or n-butylsulfonate (—$(CH_2)_4SO_3^-$). In an independent embodiment, $R^7$ and $R^{12}$ independently are hydrogen, a sulfonate-containing group, or a trialkyl amino group. In another independent embodiment, $R^7$ and $R^{12}$ are the same. In some examples, $R^7$ and $R^{12}$ are the same and are hydrogen or —$SO_3^-$ (e.g., —$SO_3^-Na^+$). In an independent embodiment, $R^5$, $R^6$, $R^8$, $R^{10}$, $R^{11}$ and $R^{13}$ are hydrogen.

Table 1 includes exemplary compounds according to formula II, in which n is 2, $R^1$ is —$CH_2$—, m is 2, $R^2$ is methyl, $R^{14}$ to $R^{17}$ are methyl, and $R^5$, $R^6$, $R^8$, $R^{10}$, $R^{11}$ and $R^{13}$ are hydrogen. Other substituents are as indicated. The maximum absorbance wavelength ($\lambda_{max}$) was measured in pH 7.4 phosphate-buffered saline.

TABLE 1

(II)

| Cpd | Z | $R^3$ | $R^4$ | $R^7$ | $R^9$ | $R^{12}$ |
|---|---|---|---|---|---|---|
| 8 | I⁻ | (benzyl ester group), $\lambda_{max}$ = 763 nm | n-Pr | H | n-Pr | H |
| 9 | I⁻ | (Fmoc-type ester group), $\lambda_{max}$ = 765 nm | n-Pr | H | n-Pr | H |

TABLE 1-continued (II)

| Cpd | Z | R³ | R⁴ | R⁷ | R⁹ | R¹² |
|---|---|---|---|---|---|---|
| 10 | I⁻ | —C(O)CH₂CH₂CH₂C(O)OH ; λ_max = 760 nm | n-Pr | H | n-Pr | H |
| 11 | I⁻ | —C(O)CH₃ ; λ_max = 760 nm | n-Pr | H | n-Pr | H |
| 12 | I⁻ | —CH₂CH₂OCH₂CH₂N⁺(CH₃)₃ I⁻ ; λ_max = 768 nm | n-Pr | H | n-Pr | H |
| 13 | Na⁺ | —C(O)CH₂CH₂CH₂C(O)O⁻Na⁺ ; λ_max = 764 nm | —(CH₂)₄SO₃Na | —SO₃Na | —(CH₂)₄SO₃Na | —SO₃Na |
| 14 | Na⁺ | —C(O)(CH₂)₅-N-maleimide ; λ_max = 766 nm | —(CH₂)₄SO₃Na | —SO₃Na | —(CH₂)₄SO₃Na | —SO₃Na |
| 15 | Na⁺ | —C(O)CH(CH₂Ph)NHBoc ; λ_max = 768 nm | —(CH₂)₄SO₃Na | —SO₃Na | —(CH₂)₄SO₃Na | —SO₃Na |

TABLE 1-continued (II) [Structure showing a heptamethine cyanine dye with two indole groups bearing R⁷, R⁴, Me, Me (left) and R¹², R⁹, Me, Me (right), connected via a cyclohexene bridge with a central O-(CH₂)₂-N(Me)-R³ ether substituent; counterion Z]

| Cpd | Z | R³ | R⁴ | R⁷ | R⁹ | R¹² |
|---|---|---|---|---|---|---|
| 24 | I⁻ | [O=C-CH(iPr)-NH-C(=O)-O-tBu group] | n-Pr | H | n-Pr | H |
| 25 | Na⁺ | [O=C-(CH₂)₃-C(=O)-O-N-succinimidyl group] | —(CH₂)₄SO₃Na | —SO₃Na | —(CH₂)₄SO₃Na | —SO₃Na |
| 26 | Na⁺ | [O=C-(CH₂)₃-N-maleimidyl group] | —(CH₂)₄SO₃Na | —SO₃Na | —(CH₂)₄SO₃Na | —SO₃Na |

The disclosed C4'-alkyl-ether Cy7 fluorophores may have a maximum absorbance wavelength in the range of from 750 to 800 nm, such as from 760-775 nm. The fluorophores may have a maximum emission wavelength in the range of from 775-850 nm, such as from 790-830 nm. The fluorophores typically have a small Stokes' shift (e.g., ~25 nm) and high extinction coefficients (100,000-250,000 $M^{-1}$ $cm^{-1}$).

Some embodiments of the disclosed C4'-alkyl-ether Cy7 fluorophores exhibit excellent stability, particularly in biological samples that may include thiols (e.g., cysteine, homocysteine, glutathione). Other known Cy7 fluorophores, such as C4' phenol- and thiol-substituted heptamethine cyanines, which are used widely, rapidly exchange with thiol nucleophiles under aqueous conditions (Zaheer et al., *Molecular Imaging* 2002, 1, 354-360). Problematic consequences have been observed during conjugation reactions with cysteine-containing peptides and macromolecules and during DNA sequencing applications, and there is one report suggesting C4' exchange reactions can occur intracellularly (Zaheer et al.; Shealy et al., *Anal. Chem.* 1995, 67, 247-251; Lim et al., *JACS* 2014 136, 7018-7025; Pascal et al., *J. Phys. Chem. A* 2014, 118, 4038-4047). In contrast, some embodiments of the disclosed C4'-alkyl-ether Cy7 fluorophores are non-reactive with biological thiols (see Example 2) and exhibit stability (e.g., as determined by substantially constant absorbance at $\lambda_{max}$) for at least 3 hours, at least 12 hours, at least one day, or at least 2 days. In one example, compound 13 was stable for at least 3 days with more than 90% of the compound remaining (i.e., the compound did not react with glutathione).

This disclosure also includes pharmaceutical compositions comprising at least one C4'-alkyl-ether Cy7 fluorophore. Some embodiments of the pharmaceutical compositions include a pharmaceutically acceptable carrier and at least one C4'-alkyl-ether Cy7 fluorophore. Useful pharmaceutically acceptable carriers and excipients are known in the art.

The pharmaceutical compositions comprising one or more C4'-alkyl-ether Cy7 fluorophores may be formulated in a variety of ways depending, for example, on the mode of administration and/or on the location to be imaged. Parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as cremophor, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The form of the pharmaceutical composition will be determined by the mode of administration chosen. Embodiments of the disclosed pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation. Generally, embodiments of the disclosed pharmaceutical compositions will be administered by injection, systemically, or orally.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. The composition may take such forms as suspension, solutions or emulsions in oily or aqueous vehicles, and may contain formulatory agents such as suspending, stabilizing and/or dispersing agents. For example, parenteral administration may be done by bolus injection or continuous infusion. Alternatively, the fluorophore may be in powder form for reconstitution with a suitable vehicle, e.g. sterile water, before use.

Systemic formulations include those designed for administration by injection, e.g., subcutaneous, intravenous, intramuscular, intrathecal or intraperitoneal injection, as well as those designed for transdermal, transmucosal, oral or pulmonary administration.

Oral formulations may be liquid (e.g., syrups, solutions or suspensions), or solid (e.g., powder, tablets, or capsules). Oral formulations may be coupled with targeting ligands for crossing the endothelial barrier. Some fluorophore formulations may be dried, e.g., by spray-drying with a disaccharide, to form fluorophore powders. Solid compositions prepared by conventional means with pharmaceutically acceptable excipients such as binding agents (e.g., pregelatinised maize starch, polyvinylpyrrolidone or hydroxypropyl methylcellulose); fillers (e.g., lactose, mannitol, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings. Actual methods of preparing such dosage forms are known, or will be apparent, to those skilled in the art.

Liquid preparations for oral administration may take the form of, for example, elixirs, solutions, syrups or suspensions. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate. Preparations for oral administration may be suitably formulated to give controlled release of the fluorophore, as is well known.

For rectal and vaginal routes of administration, the fluorophore(s) may be formulated as solutions (for retention enemas) suppositories or ointments containing conventional suppository bases such as cocoa butter or other glycerides.

For nasal administration or administration by inhalation or insufflation, the fluorophore(s) can be conveniently delivered in the form of an aerosol spray or mist from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount.

Certain embodiments of the pharmaceutical compositions comprising fluorophores as described herein may be formulated in unit dosage form suitable for individual administration of precise dosages. The pharmaceutical compositions may, if desired, be presented in a pack or dispenser device which may contain one or more unit dosage forms containing the fluorophore. The pack may, for example, comprise metal or plastic foil, such as a blister pack. The pack or dispenser device may be accompanied by instructions for administration. The amount of fluorophore administered will depend on the subject being treated, the target (e.g., the size, location, and characteristics of a tumor), and the manner of administration, and is known to those skilled in the art. Within these bounds, the formulation to be administered will contain a quantity of the fluorophore disclosed herein in an amount effective to achieve the desired visualization in the subject being treated.

IV. Methods Of Use

Embodiments of the disclosed C4'-alkyl-ether Cy7 fluorophores are useful for in vitro and in vivo applications where near-IR fluorescence is beneficial. For example, the fluorophores may be used for in vitro, in vivo, or ex vivo imaging, e.g., imaging of drug or antibody conjugates, cell identification, flow cytometry (e.g., fluorescence-activated cell sorting), and super-resolution imaging (e.g., fluorescence resonance energy transfer (FRET) imaging). Additionally, the fluorophores may be used in clinical diagnostics and surgery, such as cancer surgery where near-IR fluorescence-guided approaches to determine resection margins are emerging.

A biological sample may be contacted in vivo, ex vivo, or in vitro with a C4'-alkyl-ether Cy7 fluorophore as disclosed herein. For in vivo contact, a pharmaceutical composition comprising the C4'-alkyl-ether Cy7 fluorophore may be administered to a subject by any suitable route, e.g., intravenously or orally.

Following contact with the C4'-alkyl-ether Cy7 fluorophore, the biological sample is irradiated with near-IR radiation, and any fluorescence of the irradiated biological sample is detected. Irradiation may be performed by application of light having a desired wavelength or wavelength range within the near-IR range. In some embodiments, suitable light intensities range from 1 mW to 500 mW depending on the target site and method of application. Near-infrared light sources can be obtained from commercial sources, including Thorlabs (Newton, N.J.), Laser Components, USA (Hudson, N.H.), ProPhotonix (Salem, N.H.) and others. In some embodiments, irradiation is performed by external application of light to a targeted area. NIR light is capable of penetrating transcutaneously into tissue to a depth of several centimeters. In other embodiments, irradiation may be performed by internal application of light, such as by using an endoscope or a fiber optic catheter. Internal application may be used when the target tissue, such as a tumor, is located at a depth that is unsuitable for external light application. For example, an endoscope may be used for light delivery into the lungs, stomach, or bladder. The surface area for light application is generally selected to include target tissue, e.g., a tumor or portion of a tumor, or an area of skin external to the target tissue. When targeted application of external light is desired for an in vivo biological sample, the surface area can be controlled by use of an appropriate light applicator, such as a micro-lens, a Fresnel lens, or a diffuser arrangement. For targeted internal light application, a desired endoscope or fiber optic catheter diameter can be selected. In some applications, an indwelling catheter filled with a light scattering solution may be internally placed proximate the target tissue, and an optical fiber light source may be inserted into the catheter (see, e.g., Madsen et al., *Lasers in Surgery and Medicine* 2001, 29, 406-412).

Detection of fluorescence indicates presence of the C4'-alkyl-ether Cy7 fluorophore within the biological sample. In some embodiments, detecting fluorescence comprises obtaining a fluorescence-based image of the irradiated biological sample.

In one embodiment, a C4'-alkyl-ether Cy7 fluorophore as disclosed herein comprises a biomolecule capable of recognizing and binding directly or indirectly, in vitro, in vivo, or ex vivo, to a target (e.g., a biomarker, an antigen, a receptor) present or suspected of being present in the biological sample. The biological sample is visualized under conditions suitable to produce near-IR fluorescence if the C4'-alkyl-ether Cy7 fluorophore is present in the biological sample. The presence of the fluorophore indicates presence of the target. Excess unbound fluorophore may be removed from the biological sample (e.g., by washing a tissue sample) prior to visualizing the sample to detect fluorescence. In some embodiments, the near-IR fluorescence may be quantified to quantify the amount of target present.

In one non-limiting example, a biological sample (e.g., a bodily fluid, such as urine, blood, saliva, or mucus, or a tissue sample) that may comprise a target is contacted with a C4'-alkyl-ether Cy7 fluorophore conjugate comprising an antibody capable of recognizing and binding to the target. In another non-limiting example, a biological sample that may comprise a target is combined with a first antibody capable of recognizing and binding to the target; subsequently, the biological sample is contacted with a conjugate comprising the C4'-alkyl-ether Cy7 fluorophore and an anti-antibody antibody. In another non-limiting example, the biological sample is contacted with a C4'-alkyl-ether Cy7 fluorophore comprising a ligand capable of binding to a receptor. For instance, substituent $R^3$ of the C4'-alkyl-ether Cy7 fluorophore may include, or be conjugated to, a receptor ligand capable of binding to a receptor on a cell surface.

In one embodiment, a C4'-alkyl-ether Cy7 fluorophore as disclosed herein comprises a biomolecule capable of recognizing and binding to a tumor antigen. The biomolecule may be, for example, an antibody that recognizes and binds to the tumor antigen. The fluorophore is administered by a suitable route, e.g., by injection, to a subject with a tumor. Using near-IR fluorescence imaging, the tumor is located and visualized by its fluorescence. The fluorescence may facilitate complete excision of the tumor by enabling a user (e.g., a surgeon) to determine when the margins are clear, i.e., no fluorescence is detected after complete removal of the tumor. The fluorescence also may be used to detect and monitor tumor growth.

In another embodiment, a C4'-alkyl-ether Cy7 fluorophore as disclosed herein comprises a moiety (e.g., at $R^3$) capable of binding to or associating with a target molecule in vitro. In one non-limiting example, the moiety is an oligonucleotide capable of binding to a target nucleic acid sequence. The nucleic acid sequence may be present, for example, in a tissue sample (such as formalin-fixed, paraffin-embedded tissue) or in a gel following gel electrophoresis. The nucleic acid sequence is contacted with the C4'-alkyl-ether Cy7 fluorophore, any excess unbound fluorophore is removed, and fluorescence is detected. Fluorescence indicates presence of the target oligonucleotide sequence. In another non-limiting example, the moiety is a receptor ligand capable of binding to a target receptor. The target receptor may be present in a tissue sample. The tissue sample is contacted with the C4'-alkyl-ether Cy7 fluorophore, any excess unbound fluorophore is removed, and fluorescence is detected. Fluorescence indicates presence of the target receptor.

In an independent embodiment, a C4'-alkyl-ether Cy7 fluorophore as disclosed herein comprises a drug moiety. After administration of the C4'-alkyl-ether Cy7 fluorophore to a subject, near-IR fluorescence imaging may be used to assess the drug's location within the subject and/or to monitor drug excretion (e.g., in urine).

The foregoing examples are illustrative only, and other uses are contemplated. For example, when $R^3$ of the C4'-alkyl-ether Cy7 fluorophore comprises a hydroxy or isothiocyanate group, the fluorophore may be useful as a fluorescent tag for nucleic acids or proteins, e.g., for use during sequencing, immunoassays, or flow cytometry.

VI. Kits

Kits are also a feature of this disclosure. Embodiments of the kits include at least one compound according to general formula I. In some embodiments, the compound according to general formula I is conjugated to a biomolecule, e.g., an antibody. In some embodiments, the kits also include at least one solution in which the compound may be dissolved or suspended. The kits also may include one or more containers, such as a disposable test tube or cuvette. The kits may further include instructions for using the compound and/or for forming a conjugate comprising the compound according to general formula I and a biomolecule. In some embodiments, the kits further include reagents suitable for conjugating the compound according to general formula I to a biomolecule.

In some embodiments of the kits, the compound is provided as a solid, and the solution is provided in liquid form. The solution may be a solution suitable for dissolving the compound according to general formula I so that the dissolved compound may be administered to a subject or so that the dissolved compound may be conjugated to a biomolecule. The solution may be provided at a concentration suitable for the intended use. Alternatively, the solution may be provided as a concentrated solution, which is subsequently diluted prior to use. In certain embodiments, the compound may be premeasured into one or more containers (e.g., test tubes or cuvettes).

VI. Examples

General Materials and Methods

Unless stated otherwise, reactions were conducted in oven-dried glassware under an atmosphere of nitrogen or argon using anhydrous solvents (passed through activated alumina columns). All other commercially obtained reagents were used as received. Thin-layer chromatography (TLC) was conducted with E. Merck silica gel 60 F254 pre-coated plates (0.25 mm) and visualized by exposure to UV light (254 nm) or stained with anisaldehyde, ceric ammonium molybdate, potassium permanganate, or iodine. Flash column chromatography was performed using normal phase or reverse phase on a CombiFlash® Rf 200i (Teledyne Isco Inc.). Analytical LC/MS was performed using a Shimadzu LCMS-2020 Single Quadrupole utilizing a Kinetex 2.6 µm C18 100 Å (2.1×50 mm) column obtained from Phenomenex Inc. Runs employed a gradient of 0→90% MeCN/0.1% aqueous formic acid over 4 minutes at a flow rate of 0.2 mL/min. $^1$H NMR spectra were recorded on Bruker spectrometers (at 400 or 500 MHz) and are reported relative to deuterated solvent signals. Data for $^1$H NMR spectra are reported as follows: chemical shift (δ ppm), multiplicity, coupling constant (Hz), and integration. $^{13}$C NMR spectra were recorded on Varian spectrometers (at 100 or 125 MHz). Data for $^{13}$C NMR spectra are reported in terms of chemical shift. IR spectra were recorded on a JASCO FT/IR 4100 spectrometer and are reported in terms of frequency of absorption (cm$^{-1}$). High-resolution LC/MS analyses were conducted on a Thermo-Fisher LTQ-Orbitrap-XL hybrid mass spectrometer system with an Ion MAX API electrospray ion source in positive ion mode. Separations were carried out on a narrow-bore (50×2.1 mm), Zorbax Rapid-Resolution, reversed-phase C18 (3.5 μm) column with a flow rate of 250 μL/min with a 10 min, 2-90% gradient of MeCN/H$_2$O containing 0.1% HCOOH. Absorbance traces for quantum yield measurements were performed on a Shimadzu UV-2550 spectrophotometer operated by UVProbe 2.32 software. Fluorescence traces and quantum yield measurements were recorded on a PTI QuantaMaster steady-state spectrofluorimeter operated by FelixGX 4.0.3 software, with 10 nm excitation and emission slit widths, 0.1 s integration rate, and enabled emission correction. Data analysis and curve fitting were performed using MS Excel 2011 and GraphPad Prism 6. See *JOC Standard Abbreviations and Acronyms* for abbreviations (http://pubs.acs.org/userimages/ContentEditor/1218717864819/joceah_abbreviations.pdf).

Example 1

Syntheses and Characterization

Experimental Procedures:

(6): To a solution of IR-780 iodide 3 (100 mg, 0.150 mmol) in methyl cyanide (MeCN, 5 mL) was added N-methylethanolamine 7 (60 μL, 0.750 mmol). The solution was heated to 70° C. in a sealed vial for 2 hours as the reaction color transitioned from green to dark blue. After this time LC/MS analysis showed complete consumption of 3. The reaction mixture was concentrated in vacuo, and the residue was purified by silica gel chromatography (100% EtOAc, then 0→10% MeOH/DCM) afforded 6 (85 mg, 80%) as a dark blue iridescent solid. Compound 6 had a broad hypsochromic absorbance with a maximum at 687 nm. $^1$H NMR (CDCl$_3$, 400 MHz) δ 7.69 (d, J=13.0 Hz, 2H), 7.30 (t, J=7.5 Hz, 4H), 7.09 (d, J=7.5 Hz, 2H), 6.89 (d, J=7.9 Hz, 2H), 5.69 (d, J=13.03 Hz, 2H), 4.12-3.94 (m, 4H), 3.81 (t, J=7.4 Hz, 4H), 3.55 (s, 3H), 2.47 (t, J=6.6 Hz, 4H), 1.90-1.76 (m, 6H), 1.67 (s, 12H), 1.04 (t, J=7.4 Hz, 6H); $^{13}$C NMR (CDCl$_3$, 100 MHz) δ 176.9, 168.5, 143.0, 142.2, 140.5, 128.1, 123.5, 123.0, 122.2, 108.7, 95.0, 60.0, 59.3, 48.1, 45.3, 44.9, 29.4, 24.9, 21.9, 20.2, 11.7; IR (thin film) 1544, 1509, 1444, 1345 cm$^{-1}$; HRMS (ESI) calculated for C$_{39}$H$_{52}$N$_3$O (M$^+$) 578.4110, observed 578.4096.

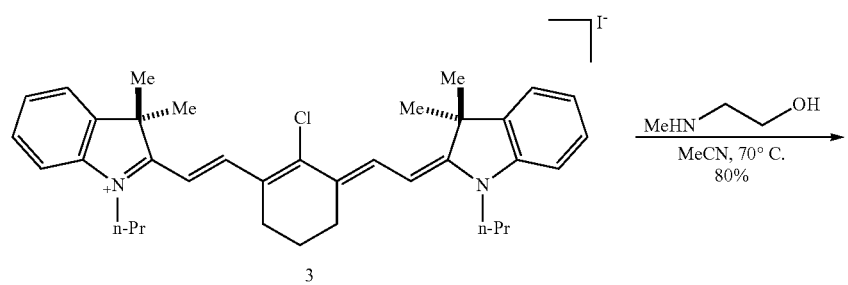

3

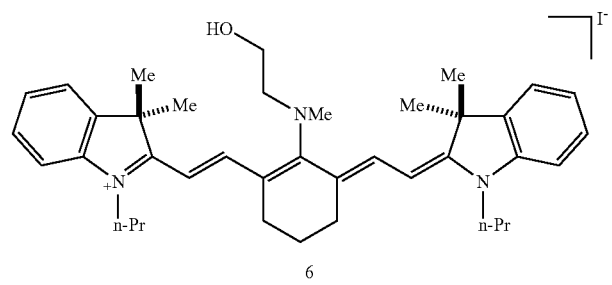

6

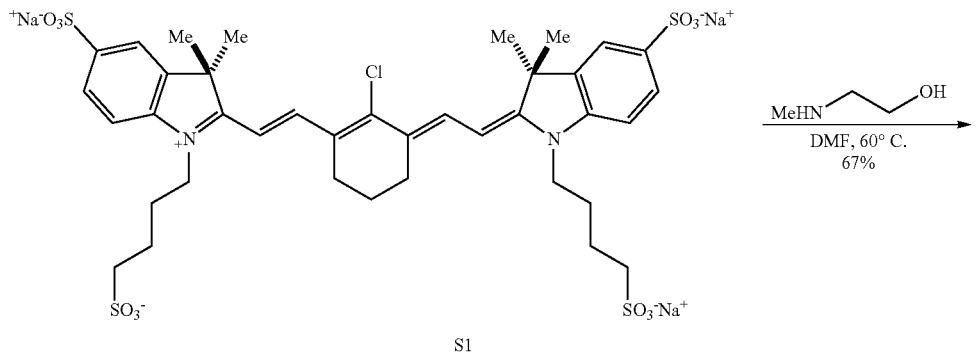

S1

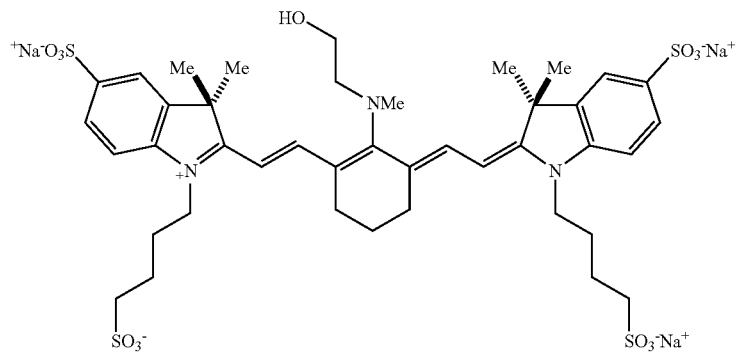

7

(7): To a solution of cyanine S1 (115 mg, 0.12 mmol; Lee et al., *J. Org. Chem.* 2006, 71, 7862-7865) in DMF (2.5 mL) was added N-methylethanolamine (190 µL, 2.41 mmol). The dark green slurry was sonicated for 5 minutes, then heated to 60° C. in a sealed vial for 45 min. After this time LC/MS analysis showed complete consumption of S1, and the reaction color had transitioned from green to dark blue. The reaction was cooled to room temperature and precipitated into Et$_2$O (100 mL) with a 1 mL DMF vial wash. The slurry was centrifuged, the supernatant discarded, and the blue pellet was resuspended in Et$_2$O (40 mL). The procedure was repeated, and the crude pellet was dissolved in 5 mL of water for an ion exchange step. A pipet was filled with 1.5 g of Dowex 50 W X8 strongly acidic 200-400 mesh resin, washed with 3 mL of water, 5 mL of 1M H$_2$SO$_4$, and finally 3 mL of water. The aqueous solution of the crude 7 was eluted (fast dropwise rate) through the Dowex column into an aqueous NaHCO$_3$ solution (200 mg in 2 mL water). After stirring for 5 minutes, this aqueous solution was purified by reversed-phase chromatography (0→10% MeCN/water) to afford 7 (80 mg, 67%) as a dark blue solid. Compound 7 had a broad hypsochromic absorbance with $\lambda_{max}$ 644 nm (2 µM in PBS, pH 7.4). $^1$H NMR (CD$_3$OD, 400 MHz) δ 7.85-7.77 (m, 4H), 7.73 (d, J=13.2 Hz, 2H), 7.16 (d, J=8.3 Hz, 2H), 5.97 (d, J=13.2 Hz, 2H), 4.10-3.89 (m, 7H), 3.54 (s, 3H), 2.97-2.81 (m, 4H), 2.57 (t, J=6.6 Hz, 4H), 2.03-1.78 (m, 10H), 1.67 (s, 12H); $^{13}$C NMR (DMSO-d$_6$, 100 MHz) δ 175.9, 167.6, 143.2, 142.9, 141.0, 139.4, 125.9, 123.4, 119.4, 108.5, 95.5, 59.8, 58.6, 50.8, 47.3, 44.2, 42.7, 39.5, 28.7, 25.5, 24.3, 22.6, 21.5; IR (thin film) 3412, 1545, 1515, 1478, 1378, 1285 cm$^{-1}$; HRMS (ESI) calculated for C$_{41}$H$_{52}$N$_3$O$_{13}$S$_4$; (M−3H$^{-3}$) 307.4122, observed 307.4134.

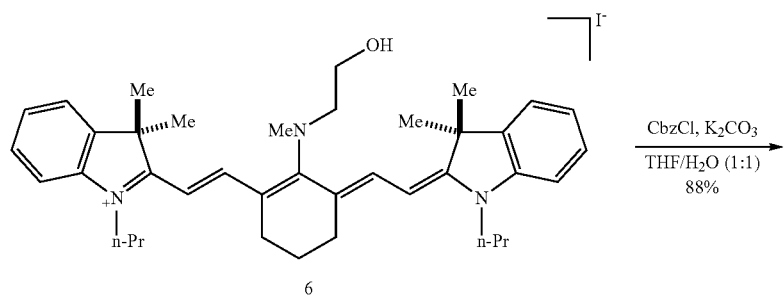

6

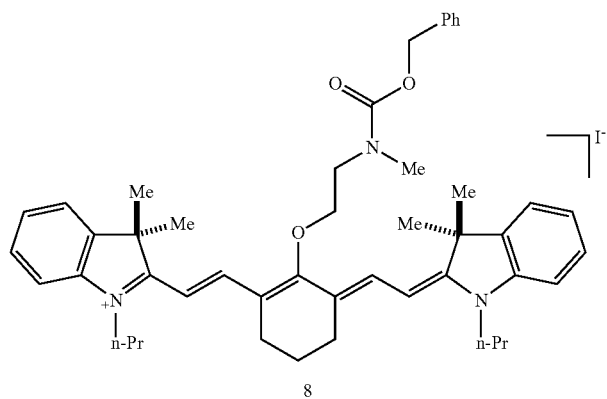

8

(8): To a solution of 6 (50 mg, 0.072 mmol; Gorka et al., J. Am. Chem. Soc. dx.doi.org/10.1021/ja5065203) in 1:1/ THF:H$_2$O (1 mL) was added benzyl chloroformate (CbzCl, 30 μL, 0.217 mmol) and potassium carbonate (50 mg, 0.362 mmol). The biphasic solution was stirred at room temperature for two hours as the reaction color transitioned from dark blue to green. After this time LC/MS analysis showed complete consumption of 6. The solution was diluted with saturated aqueous sodium iodide (10 mL), extracted with dichloromethane (2×10 mL), and dried over Na$_2$SO$_4$. The solvent removed in vacuo, and the residue was purified by silica gel chromatography (0→25% MeOH/DCM) affording 8 (54 mg, 88%)) as an iridescent green solid. $\lambda_{max}$ 763 nm (2 μM in 0.1 M PBS, pH 7.4, with 20% DMSO (v/v), FIG. 1A). $^1$H NMR (400 MHz, CD$_3$CN, 70° C.) δ 8.10 (d, J=14.2 Hz, 2H), 7.54-7.14 (m, 13H), 6.09 (d, J=14.2 Hz, 2H), 5.16 (s, 2H), 4.15 (t, J=5.7 Hz, 2H), 4.02 (t, J=7.4 Hz, 4H), 3.87 (t, J=5.7 Hz, 2H), 3.14 (s, 3H), 2.61 (t, J=6.2 Hz, 4H), 1.92-1.80 (m, 6H), 1.66 (s, 12H), 1.03 (t, J=7.4 Hz, 6H). $^{13}$C NMR (100 MHz, CD$_3$CN, 70° C.) δ 173.6, 171.8, 157.6, 144.1, 142.6, 142.1, 138.7, 129.9, 129.8, 129.2, 129.0, 126.1, 124.3, 123.6, 112.2, 100.9, 76.8, 68.3, 50.8, 50.4, 46.9, 36.9, 29.0, 25.8, 22.4, 21.8, 11.9. IR (thin film) 1698, 1553, 1505, 1361, 1248 cm$^{-1}$; HRMS (ESI) calculated for C$_{47}$H$_{58}$N$_3$O$_3$ (M$^+$) 712.4473, observed 712.4446. Compound 8 exhibited a bathochromic shifted $\lambda_{max}$ relative to N-linked 6, a small Stokes shift ($\lambda_{ex}$=774 nm, $\lambda_{em}$=797 nm), and a high absorbance coefficient (ε=187,000 M$^{-1}$cm$^{-1}$).

TABLE 2

Table 2 provides 2D-NMR data for compound 8 using the below numbering scheme:

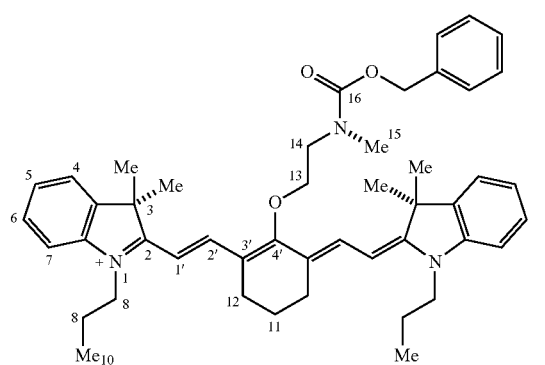

8

$^1$H (400 MHz), $^{13}$C (100 MHz), HMBC, and COSY NMR data for 8, CD$_3$CN, 45° C.

| atom | $^{13}$C (mult) | $^1$H mult, J (Hz) | HMBC[a] | COSY[b] |
|---|---|---|---|---|
| 1' | 100.6 (CH) | 6.08 (d, J = 14.2 Hz, 2H) | 2, 2', 3 | 2' |
| 2' | 141.7 (CH) | 8.07 (d, J = 14.2 Hz, 2H) | 4', 12 | 1' |
| 3' | 123.9 (C) | | | |
| 4' | 171.3 (C) | | | |
| 11 | 22.2 (CH$_2$) | 1.91-1.78 (m, 2H) | 3', 12 | 12 |
| 12 | 25.5 (CH$_2$) | 2.59 (t, J = 6.1 Hz, 4H) | 2', 3', 4', 11 | 11 |
| 13 | 76.6 (CH$_2$) | 4.11 (t, J = 5.5 Hz, 2H) | 4', 14 | 14 |
| 14 | 50.1 (CH$_2$) | 3.86 (t, J = 5.5 Hz, 2H) | 13, 15, 16 | 13 |

[a]Carbons that correlate to the proton resonance. Optimized for 10 Hz coupling.
[b]Protons that correlate to the proton resonance.

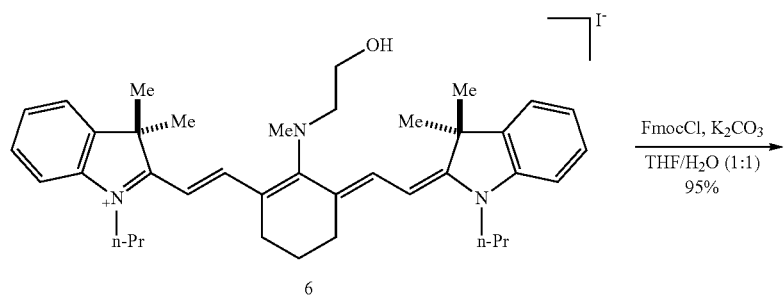

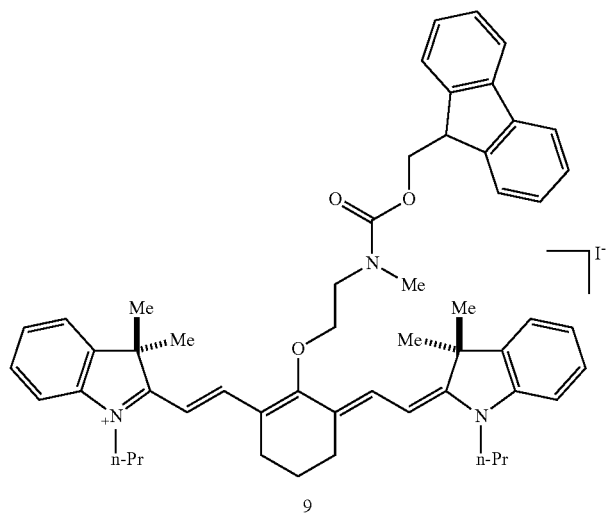

Figure 1B:
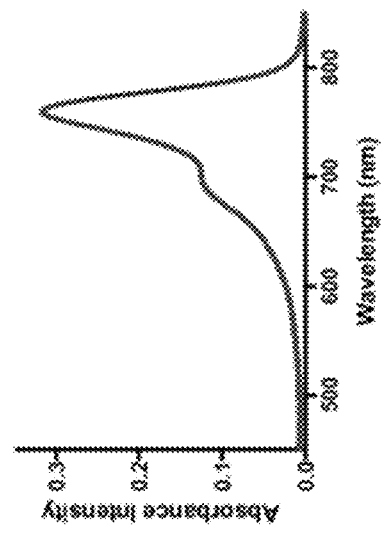

(9): To a solution of 6 (38 mg, 0.054 mmol) in 1:1/THF: H₂O (1 mL) was added 9-fluorenylmethyl chloroformate (FmocCl, 42 mg, 0.16 mmol) and potassium carbonate (37 mg, 0.27 mmol). The biphasic solution was stirred vigorously at room temperature for 15 minutes as the reaction color transitioned from dark blue to green. After this time LC/MS analysis showed complete consumption of 6. The solution was diluted with saturated aqueous sodium iodide (10 mL), extracted with dichloromethane (2×10 mL), and dried over Na₂SO₄. The solvent was removed in vacuo, and the residue was purified by silica gel chromatography (0→10% MeOH/DCM) affording 9 (48 mg, 95%) as an iridescent green solid. $\lambda_{max}$ 765 nm (2 μM in 0.1 M PBS, pH 7.4, with 20% DMSO (v/v), FIG. 1B). ¹H NMR (400 MHz, CD₃CN, 70° C.) δ 8.02 (d, J=14.2 Hz, 2H), 7.84-7.74 (m, 2H), 7.68-7.58 (m, 2H), 7.43-7.19 (m, 12H), 6.08 (d, J=14.2 Hz, 2H), 4.48 (d, J=6.0 Hz, 2H), 4.27 (t, J=6.0 Hz, 1H), 4.02 (t, J=7.4 Hz, 4H), 3.98-3.82 (m, 2H), 3.77-3.59 (m, 2H), 3.05 (s, 3H), 2.61 (t, J=6.2 Hz, 4H), 1.91-1.79 (m, 6H), 1.61 (s, 12H), 1.02 (t, J=7.4 Hz, 5H). IR (thin film) 1699, 1553, 1505, 1393, 1362, 1246 cm⁻¹; HRMS (ESI) calculated for C₅₄H₆₂N₃O₃ (M⁺) 800.4786, observed 800.4781.

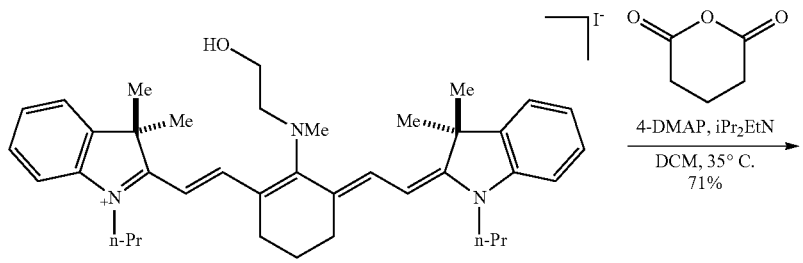

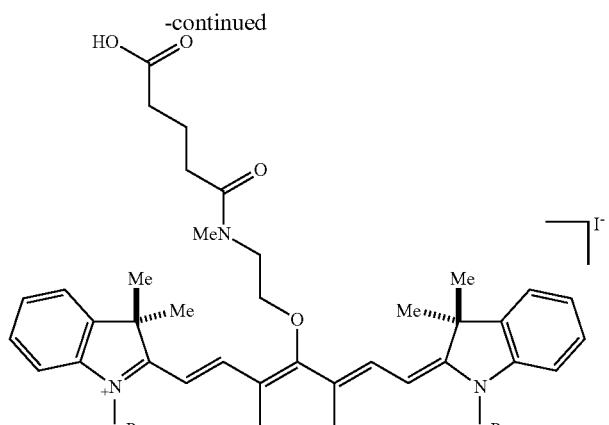

10

Figure 1C:
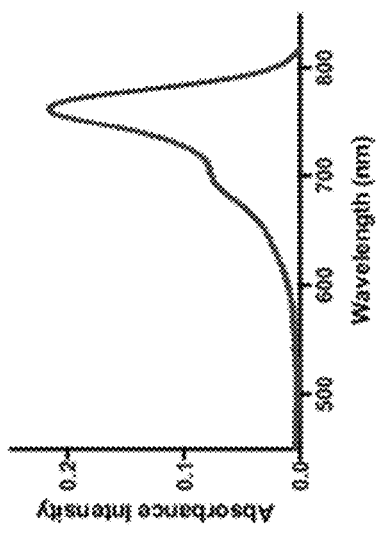

(10): To a solution of 6 (200 mg, 0.28 mmol) in DCM (5 mL) was added 4-dimethylaminopyridine (DMPA, 10 mg, 0.084), diisopropylethylamine (iPr$_2$EtN, 100 μL, 0.56 mmol) and glutaric anhydride (50 mg, 0.43 mmol). The reaction was heated to 35° C. in a sealed vial for 18 hours, during which time the reaction color transitioned from green to dark blue. After this time LC/MS analysis showed complete consumption of 6. The reaction was diluted with saturated aqueous sodium iodide (10 mL), extracted with dichloromethane (2×10 mL), and dried over Na$_2$SO$_4$. The solvent was removed in vacuo and the green residue was purified by silica gel chromatography (0→30% MeOH/DCM) to afford 10 (165 mg, 71%) as an iridescent green solid. λ$_{max}$ 760 nm (2 μM in 0.1 M PBS, pH 7.4, with 0.1% DMSO (v/v), FIG. 1C). $^1$H NMR (CD$_3$CN, 400 MHz, 70° C.) δ 8.12 (d, J=14.0 Hz, 2H), 7.51 (d, J=7.4 Hz, 2H), 7.41 (m, 2H), 7.29-7.21 (m, 4H), 6.11 (d, J=14.0 Hz, 2H), 4.13 (t, J=6.0 Hz, 2H), 4.03 (t, J=7.4 Hz, 4H), 3.92 (t, J=6.0 Hz, 2H), 3.18 (br s, 3H), 2.62 (t, J=6.0 Hz, 4H), 2.44-2.36 (m, 2H), 2.34 (t, J=7.3 Hz, 2H), 1.92-1.81 (m, 8H), 1.72 (s, 12H), 1.07-1.00 (t, J=7.4 Hz, 6H). IR (thin film) 1723, 1634, 1552, 1506, 1366, 1250 cm$^{-1}$; HRMS (ESI) calculated for C$_{44}$H$_{58}$N$_3$O$_4$ (M$^+$) 692.4422, observed 692.4405.

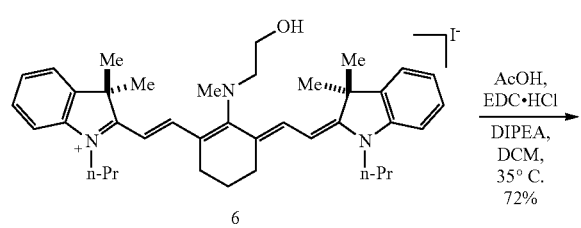

6

AcOH,
EDC•HCl
─────────→
DIPEA,
DCM,
35° C.
72%

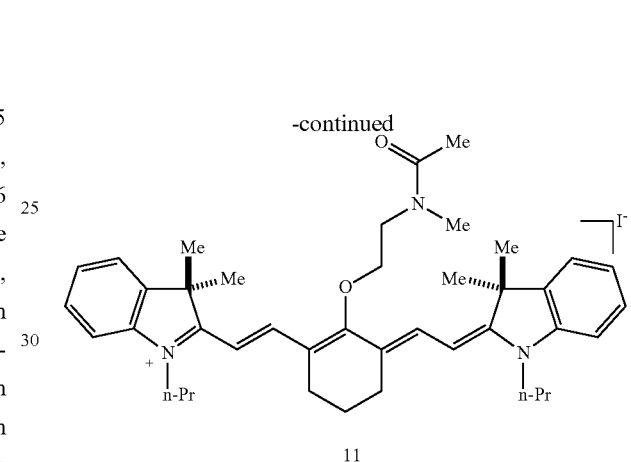

11

Figure 1D:
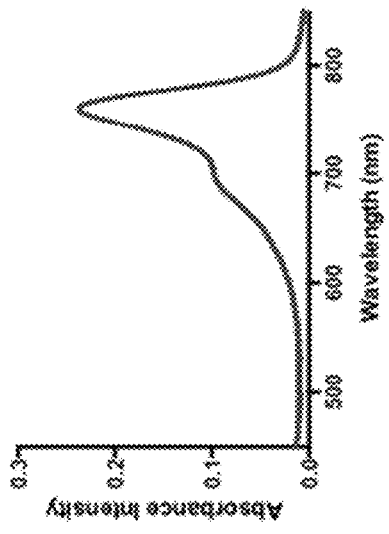

(11): To a solution of 6 (30 mg, 0.043 mmol), acetic acid (AcOH, 5 μL, 0.09 mmol), and N,N-diisopropylethylamine (DIPEA, 12 μL, 0.090 mmol) in DCM (2 mL) was added 1-ethyl-3-(3-dimethylaminopropyl)carbodiimide.HCl (EDC.HCl, 16 mg, 0.090 mmol) at room temperature. The reaction was heated to 35° C. in a sealed vial for 18 hours, during which time the reaction color transitioned from dark blue to green. After this time LC/MS analysis showed complete consumption of 6. The reaction was diluted with saturated aqueous sodium iodide (10 mL), extracted with dichloromethane (2×10 mL), and dried over Na$_2$SO$_4$. The solvent was removed in vacuo and the green residue was purified by silica gel chromatography (0→30% MeOH/DCM) affording 23 mg (72%) of 11 as an iridescent green solid. λ$_{max}$ 760 nm (2 μM in 0.1 M PBS, pH 7.4, with 0.1% DMSO (v/v), FIG. 1D). $^1$H NMR (400 MHz, CD$_3$CN, 75° C.) δ 8.11 (d, J=14.2 Hz, 2H), 7.48 (d, J=7.3 Hz, 2H), 7.40 (td, J=7.8, 1.2 Hz, 2H), 7.30-7.19 (m, 4H), 6.10 (d, J=14.2 Hz, 2H), 4.19-4.07 (m, 2H), 4.03 (t, J=7.4 Hz, 4H), 3.89 (t, J=5.9 Hz, 2H), 3.24-3.04 (m, 3H), 2.61 (t, J=6.0 Hz, 4H), 2.23-2.07 (m, 3H), 1.91-1.80 (m, 6H), 1.71 (br s, 12H), 1.03 (t, J=7.4 Hz, 6H); IR (thin film) 1634, 1553, 1505, 1394, 1365, 1248 cm$^{-1}$; HRMS (ESI) calculated for C$_{41}$H$_{54}$N$_3$O$_2$ (M$^+$) 620.4211, observed 620.4200.

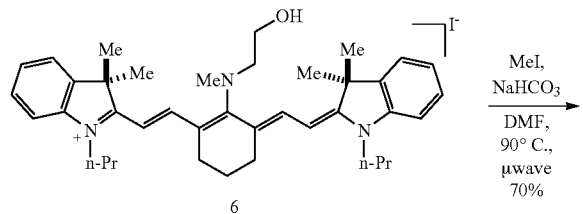

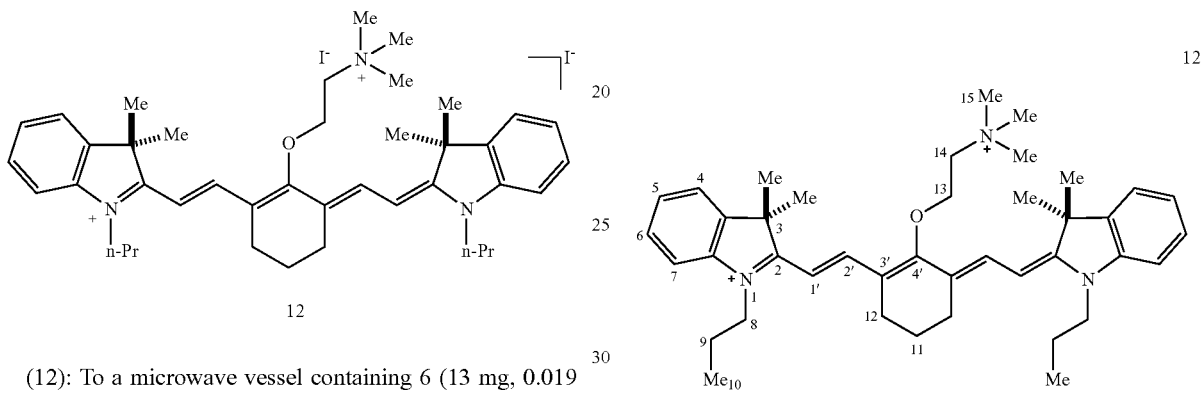

Figure 1E:
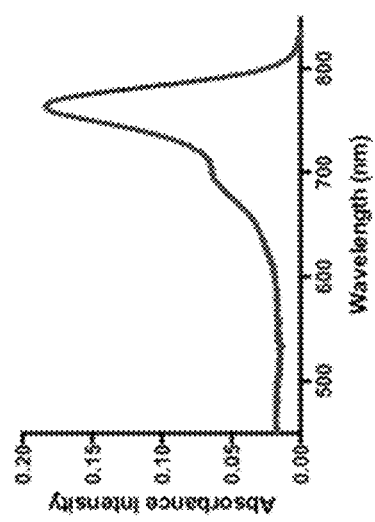

(12): To a microwave vessel containing 6 (13 mg, 0.019 mmol) in dimethylformamide (0.5 mL) was added methyl iodide (MeI, 17 μL, 0.28 mmol) and NaHCO$_3$ (15 mg, 0.28 mmol). The vessel was sealed, purged with argon, and subjected to 90° C. microwave irradiation for 8 hours, during which time the reaction color transitioned from dark blue to green. After this time LC/MS analysis showed complete consumption of 6. The reaction was precipitated into diethyl ether (10 mL), centrifuged, and decanted to afford a green residue. The crude material was purified by silica gel chromatography (0→30% MeOH/DCM) to afford 12 (11 mg, 70%) as a green iridescent solid. $\lambda_{max}$ 768 nm (2 μM in 0.1 M PBS, pH 7.4, with 0.1% DMSO (v/v), FIG. 1E). $^1$H NMR (CD$_3$OD, 400 MHz) δ 8.02 (d, J=14.0 Hz, 2H), 7.54 (d, J=7.4 Hz, 2H), 7.39 (t, J=7.7 Hz, 2H), 7.31 (d, J=8.0 Hz, 2H), 7.24 (t, J=7.4 Hz, 2H), 6.19 (d, J=14.0 Hz, 2H), 4.59 (t, J=6.2 Hz, 2H), 4.14 (m, 6H), 3.49 (s, 9H), 2.65 (m, 4H), 1.87 (m, 6H), 1.76 (s, 12H), 1.04 (t, J=7.4 Hz, 6H); $^{13}$C NMR (CD$_3$OD, 100 MHz) δ 173.2, 170.2, 143.8, 142.4, 141.0, 129.8, 126.1, 124.0, 123.5, 112.1, 101.3, 70.9, 66.4, 55.3, 50.4, 46.6, 29.1, 25.9, 22.1, 21.8, 11.8; IR (thin film) 1552, 1503, 1393, 1362, 1247 cm$^{-1}$; HRMS (ESI) calculated for C$_{41}$H$_{57}$N$_3$O (M$^{+2}$) 303.7245, observed 303.7247.

Table 3 provides 2D-NMR data for compound 12 using the below numbering scheme:

TABLE 3

$^1$H (400 MHz), $^{13}$C (100 MHz), HMBC, and COSY NMR data for 12, CD$_3$OD

| atom | $^{13}$C (mult) | $^1$H mult, J (Hz) | HMBC[a] | COSY[b] |
|---|---|---|---|---|
| 1' | 101.3 (CH) | 6.20 (d, J = 14.2 Hz, 2H) | 2, 2', 3, 3' | 2' |
| 2' | 141.0 (CH) | 8.03 (d, J = 14.2 Hz, 2H) | 2, 4', 12 | 1' |
| 3' | 124.0 (C) | | | |
| 4' | 170.2 (C) | | | |
| 11 | 22.1 (CH$_2$) | 1.97-1.91 (m, 2H) | 3', 12 | 12 |
| 12 | 25.9 (CH$_2$) | 2.75-2.57 (m, 4H) | 2', 3', 4', 11 | 11 |
| 13 | 70.9 (CH$_2$) | 4.60 (t, J = 6.2 Hz, 2H) | 4', 14 | 14 |
| 14 | 66.4 (CH$_2$) | 4.23-4.07 (m, 2H) | 13, 15 | 13 |

[a]Carbons that correlate to the proton resonance. Optimized for 10 Hz coupling.
[b]Protons that correlate to the proton resonance.

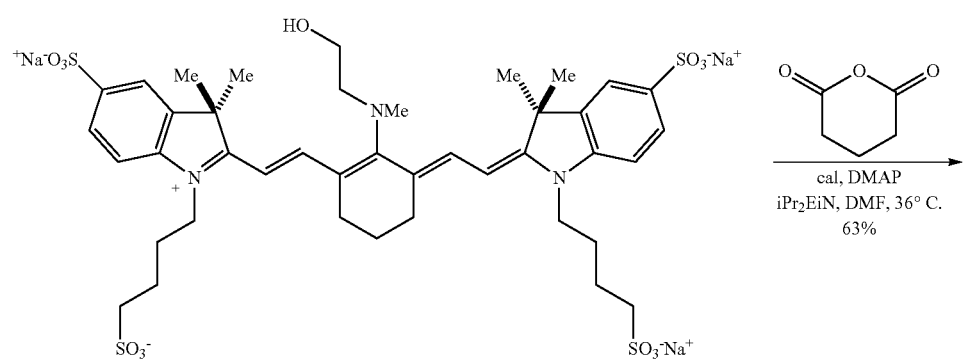

-continued

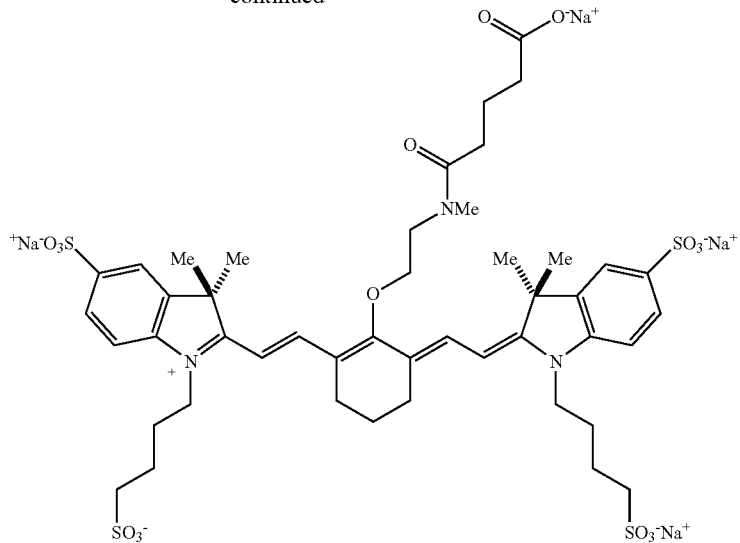

13

Figure 1F:
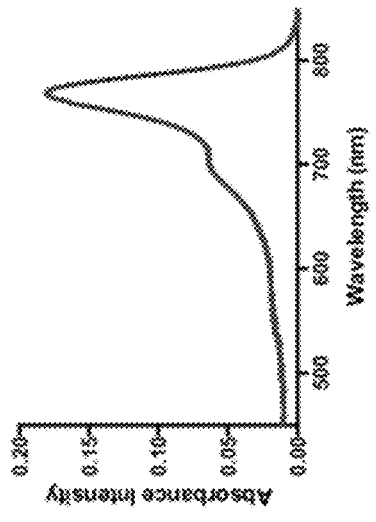

(13): To a solution of 7 (55 mg, 0.055 mmol) in DMF (0.5 mL) was added 4-dimethylaminopyridine (0.4 mg, 0.003), diisopropylethylamine (29 μL, 0.17 mmol) and glutaric anhydride (19 mg, 0.17 mmol). The slurry was heated to 35° C. in a sealed vial for 3 hours, during which time the reaction became homogeneous and dark green. After this time LC/MS analysis showed complete consumption of 7. The reaction was cooled to room temperature and precipitated into Et$_2$O (40 mL) with a 1 mL DMF vial wash. The slurry was centrifuged, the supernatant discarded, and the green pellet was resuspended in Et$_2$O (20 mL). The procedure was repeated, and the crude was purified by reversed-phase chromatography (0→20% MeCN/0.1% v/v aqueous formic acid). The solvent was evaporated, and the crude material was dissolved in 5 mL of water for an ion exchange step. A pipet was filled with 1.5 g of Dowex 50 W X8 strongly acidic 200-400 mesh resin, washed with 3 mL of water, 5 mL of 1M H$_2$SO$_4$, and finally 3 mL of water. The aqueous solution of the crude 13 was eluted (fast dropwise rate) through the Dowex column into an aqueous NaHCO$_3$ solution (250 mg in 3 mL water). After stirring for 5 minutes, this aqueous solution was purified by reversed-phase chromatography (0→20% MeCN/water) to afford 13 (39 mg, 63%) as a dark green solid. λ$_{max}$ 764 nm (2 μM in 0.1 M PBS, pH 7.4, with 0.1% DMSO (v/v), FIG. 1F). $^1$H NMR (CD$_3$OD, 500 MHz, compound exists as a mixture of rotamers; major rotamer is designated by *, minor rotamer denoted by §)δ 8.18 (d, J=14.2 Hz, 1H*), 8.14 (d, J=14.2 Hz, 1H$^§$), 7.96-7.91 (m, 2H*, 2H$^§$), 7.89 (d, J=8.4 Hz, 2H*, 2H$^§$), 7.39-7.32 (m, 2H*, 2H$^§$), 6.30-6.21 (m, 2H*, 2H$^§$), 4.26-4.10 (m, 6H*, 6H$^§$), 4.04 (t, J=4.5 Hz, 1H$^§$), 3.97 (t, J=4.5 Hz, 1H*), 3.28 (s, 3H*), 3.23 (s, 3H$^§$), 2.90 (t, J=6.7 Hz, 4H*, 4H$^§$), 2.71-2.64 (m, 4H*, 4H$^§$), 2.58 (t, J=7.7 Hz, 2H$^§$), 2.53 (t, J=7.7 Hz, 2H*), 2.26 (t, J=7.2 Hz, 2H*), 2.22 (t, J=7.2 Hz, 2H$^§$), 2.05-1.86(m, 12H*, 12H$^§$), 1.77 (s, 12H*), 1.74 (s, 12H$^§$); IR (thin film) 1723, 1641, 1555, 1503, 1361, 1233 cm$^{-1}$; HRMS (ESI) calculated for C$_{46}$H$_{58}$N$_3$O$_{16}$S$_4$; (M-3H$^{-3}$) 345.4228, observed 345.4244.

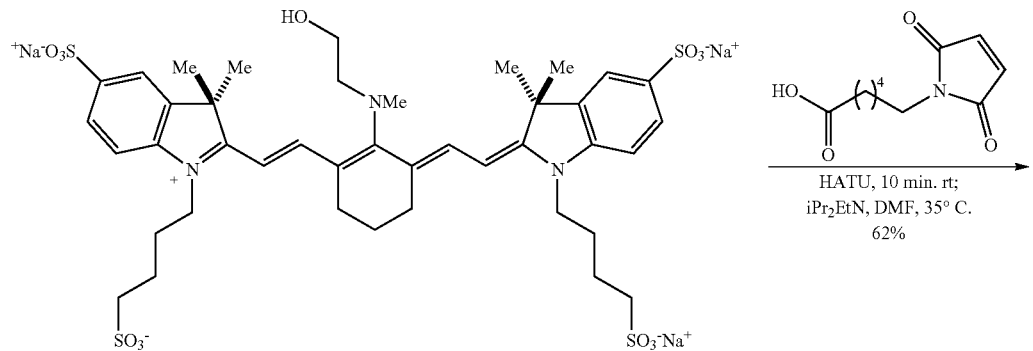

7

-continued

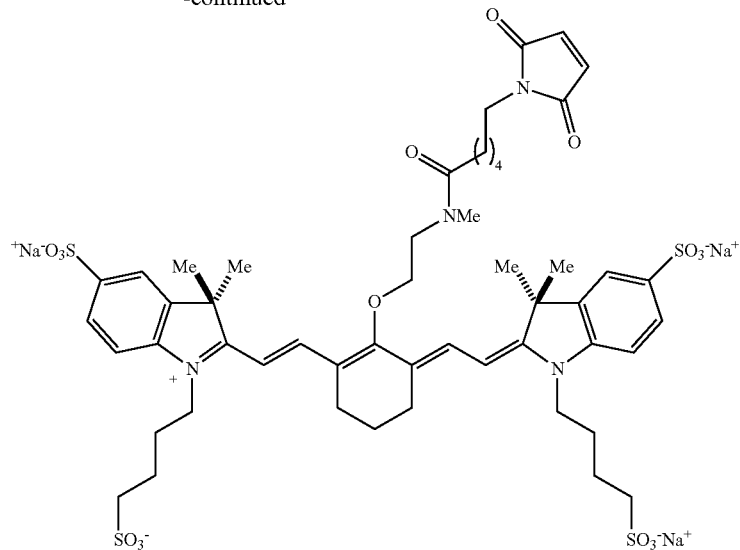

14

Figure 1G:
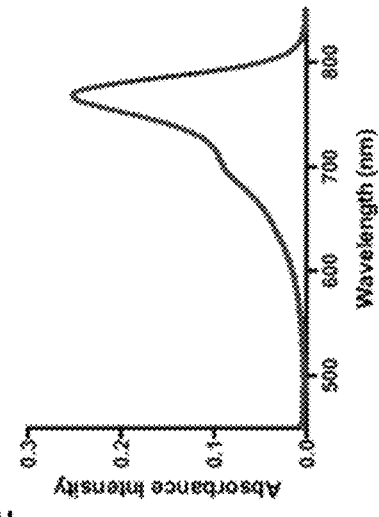

(14): 6-Maleimidohexanoic acid (12 mg, 0.058 mmol) and HATU (N-[(dimethylamino)-1H-1,2,3-triazolo-[4,5-b]pyridin-1-ylmethylene]-N-methylmethanaminium hexafluorophosphate N-oxide, 22 mg, 0.058 mmol) were charged to a 1-dram vial. DMF (0.4 mL) and diisopropylethylamine (15 µL, 0.088 mmol) were added to the vial under argon, and the resulting homogeneous light yellow solution was stirred at room temperature for 10 min. This activated ester/DMF solution was then transferred to a vial containing 7 (29 mg, 0.029 mmol) and DMF (0.4 mL). The deep blue slurry was heated to 35° C. for 1.5 hours, as the reaction color transitioned to green, and after which LC/MS analysis showed complete consumption of 7. The reaction was cooled to room temperature and precipitated into $Et_2O$ (40 mL) with a 1 mL DMF vial wash. The slurry was centrifuged, the supernatant discarded, and the green pellet was resuspended in $Et_2O$ (20 mL). The procedure was repeated, and the crude material was dissolved in 5 mL of water for an ion exchange step. A pipet was filled with 1.5 g of Dowex 50 W X8 strongly acidic 200-400 mesh resin, washed with 3 mL of water, 5 mL of 1M $H_2SO_4$, and finally 3 mL of water. The aqueous solution of the crude 14 was eluted (fast dropwise rate) through the Dowex column into an aqueous $NaHCO_3$ solution (100 mg in 2 mL water). After stirring for 5 minutes, this aqueous solution was purified by reversed-phase chromatography (0→15% MeCN/water) to afford 14 (21 mg, 62%) as a dark green solid. $\lambda_{max}$ 766 nm (2 µM in 0.1 M PBS, pH 7.4, with 0.1% DMSO (v/v), FIG. 1G). $^1$H NMR ($CD_3OD$, 400 MHz, compound exists as a mixture of rotamers, major rotamer is designated by *, minor rotamer denoted by §)δ 8.18 (d, J=14.1 Hz, 2H*), 8.12 (d, J=14.1 Hz, 2H$^§$), 7.96-7.86 (m, 4H*, 4H$^§$), 7.44-7.30 (m, 2H*, 2H$^§$), 6.79 (s, 2H*), 6.76 (s, 2H$^§$), 6.32-6.18 (m, 2H*, 2H$^§$), 4.26-4.10 (m, 6H*, 6H$^§$), 4.05-3.94 (m, 2H*, 2H$^§$), 3.52 (t, J=6.9 Hz, 2H*), 3.44 (t, J=6.9 Hz, 2H$^§$), 3.29 (s, 3H*), 3.18 (s, 3H$^§$), 2.90 (t, J=6.8 Hz, 4H*, 4H$^§$), 2.71-2.67 (m, 4H*, 4H$^§$), 2.61 (t, J=7.5 Hz, 2H*), 2.50 (t, J=7.4 Hz, 2H*), 2.06-1.88 (m, 10H*, 10H$^§$), 1.77 (s, 12H*), 1.74 (s, 12H$^§$), 1.72-1.51 (m, 4H*, 4H$^§$), 1.42-1.26 (m, 2H*, 2H$^§$); IR (thin film) 1701, 1636, 1554, 1507, 1394, 1359, 1254 $cm^{-1}$; HRMS (ESI) calculated for $C_{51}H_{63}N_4O_{16}S_4$; (M-3H$^{-3}$) 371.7702, observed 371.7720.

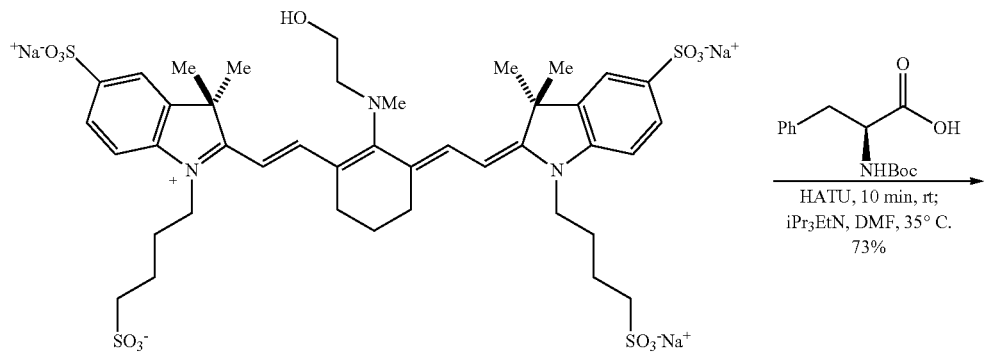

7

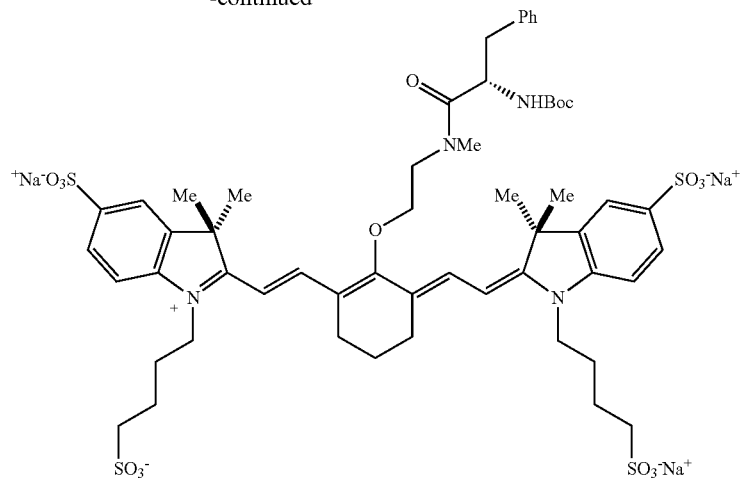

15

Figure 1H:
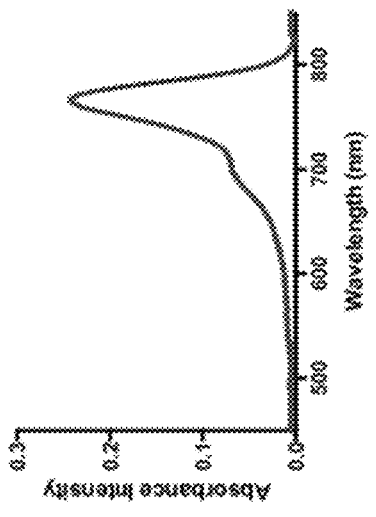

(15): Boc-L-phenylalanine (12 mg, 0.046 mmol) and HATU (17 mg, 0.046 mmol) were charged to a 1-dram vial. DMF (0.4 mL) and diisopropylethylamine (12 µL, 0.069 mmol) were added to the vial under argon, and the resulting homogeneous light yellow solution was stirred at room temperature for 10 min. This activated ester/DMF solution was then transferred to a vial containing 7 (23 mg, 0.023 mmol) and DMF (0.4 mL). The deep blue slurry was heated to 35° C. for 1.5 hours as the reaction color transitioned to green, at which point LC/MS analysis showed complete consumption of 7. The reaction was cooled to room temperature and precipitated into Et$_2$O (40 mL) with a 1 mL DMF vial wash. The slurry was centrifuged, the supernatant discarded, and the blue pellet was resuspended in Et$_2$O (20 mL). The procedure was repeated, and the crude material was dissolved in 5 mL of water for an ion exchange step. A pipet was filled with 1.5 g of Dowex 50 W X8 strongly acidic 200-400 mesh resin, washed with 3 mL of water, 5 mL of 1M H$_2$SO$_4$, and finally 3 mL of water. The aqueous solution of the crude 15 was eluted (fast dropwise rate) through the Dowex column into an aqueous NaHCO$_3$ solution (80 mg in 2 mL water). After stirring for 5 minutes, this aqueous solution was purified by reversed-phase chromatography (0→20% MeCN/water) to afford 15 (21 mg, 73%) as a dark green solid. $\lambda_{max}$ 768 nm (2 µM in 0.1 M PBS, pH 7.4, with 0.1% DMSO (v/v), FIG. 1H). $^1$H NMR (CD$_3$OD, 500 MHz, compound exists as a mixture of rotamers, major rotamer is designated by *, minor rotamer denoted by §) δ 8.16 (d, J=14.0 Hz, 2H$^§$), 8.09 (d, J=14.0 Hz, 2H*), 7.94-7.83 (m, 4H*, 4H$^§$), 7.37 (d, J=8.3 Hz, 2H*, 2H$^§$), 7.32-7.09 (m, 4H*, 4H$^§$), 6.31-6.20 (m, 2H*, 2H$^§$), 5.00-4.95 (m, 1H*), 4.82-4.78 (m, 1H$^§$), 4.24-4.14 (m, 4H*, 4H$^§$), 4.15-3.60 (m, 4H*, 4H$^§$), 3.15 (s, 3H*), 3.03 (s, 3H$^§$), 3.00-2.85 (m, 6H*, 6H$^§$), 2.76-2.62 (m, 4H*, 4H$^§$), 2.06-1.87 (m, 10H*, 10H$^§$), 1.84-1.32 (m, 21H*, 21H$^§$); IR (thin film) 1701, 1643, 1555, 1507, 1394, 1361, 1255 cm$^{-1}$; HRMS (ESI) calculated for C$_{55}$H$_{69}$N$_3$O$_{16}$S$_4$; (M−3H$^{-3}$) 389.7858, observed 389.7875.

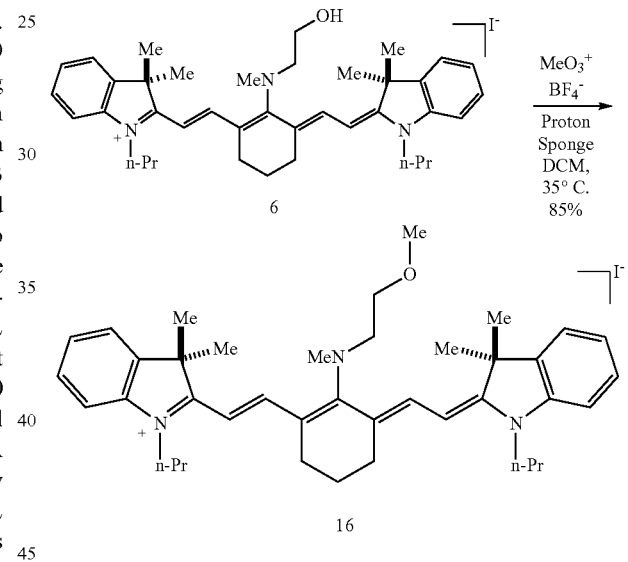

(16): To a mixture of MeO$_3^+$BF$_4^-$ (38 mg, 0.26 mmol) and 1,8-bis(dimethyl-amino)naphthalene (Proton Sponge®, Sigma-Aldrich, 16 mg, 0.052 mmol) in DCM (0.5 mL) under argon was added a solution of 6 (36 mg, 0.052 mmol) in DCM (2 mL) at room temperature. The blue reaction was heated to 35° C. for 2 hours, at which time LC/MS analysis showed complete consumption of 6. The reaction was quenched with saturated aqueous NaHCO$_3$ (10 mL) and extracted with dichloromethane (15 mL). The organic layer was washed with saturated aqueous sodium iodide (2×5 mL) and dried over Na$_2$SO$_4$. The solvent was removed in vacuo and the blue residue was purified by silica gel chromatography (0→10% MeOH/DCM) affording 31 mg (85%) of 16 as an iridescent blue solid. $\lambda_{max}$ 668 nm (2 µM in 0.1 M PBS, pH 7.4, with 0.1% DMSO (v/v), FIG. 1I). $^1$H NMR (500 MHz, CDCl$_3$) δ 7.60 (d, J=13.4 Hz, 2H), 7.34-7.27 (m, 4H), 7.10 (t, J=7.5 Hz, 2H), 6.95 (d, J=7.9 Hz, 2H), 5.76 (d, J=13.4 Hz, 2H), 3.96 (t, J=4.9 Hz, 2H), 3.86 (t, J=7.3 Hz, 4H), 3.78 (t, J=5.0 Hz, 2H), 3.48 (s, 3H), 3.39 (s, 3H), 2.46 (t, J=6.5 Hz, 4H), 1.91-1.78 (m, 6H), 1.64 (s, 12H), 1.04 (t, J=7.4 Hz, 6H); $^{13}$C NMR (125 MHz, CDCl$_3$) δ 175.7, 168.7, 142.9, 142.2, 140.3, 128.3, 123.6, 123.3, 122.1, 109.1, 95.5, 70.1, 58.7, 57.2, 48.0, 45.0, 45.0, 29.1, 24.7, 21.8, 20.3, 11.7. IR (thin film) 1547, 1506, 1449, 1343, 1252 cm$^{-1}$; HRMS (ESI) calculated for $C_{40}H_{54}N_3O$ (M$^+$) 592.4261, observed 592.4246.

This example demonstrated that, consistent with a requirement for initial N-activation, different methylation conditions produced divergent reaction pathways. While methyl iodide yielded the desired rearrangement product (compound 12), trimethyloxonium tetrafluoroborate afforded instead the methyl ether 16 without the desired rearrangement.

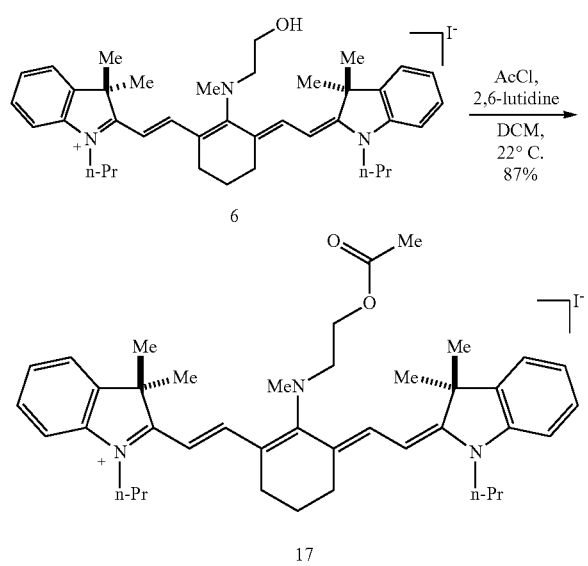

LC/MS analysis showed complete consumption of 6. The solution was diluted with saturated aqueous sodium iodide (5 mL), extracted with dichloromethane (2×10 mL), and the organic layer dried over $Na_2SO_4$. The solvent was removed in vacuo, and the blue residue was purified by silica gel chromatography (0→10% MeOH/DCM) affording 28 mg (87%) of 17 as an iridescent blue solid. $\lambda_{max}$ 689 nm (2 μM in 0.1 M PBS, pH 7.4, with 0.1% DMSO (v/v), FIG. 1J). $^1$H NMR (400 MHz, CD$_3$CN) δ 7.62 (d, J=13.6 Hz, 2H), 7.46-7.38 (d, J=7.3 Hz, 2H), 7.33 (td, J=7.7, 1.2 Hz, 2H), 7.19-7.07 (m, 4H), 5.92 (d, J=13.6 Hz, 2H), 4.31 (t, J=5.0 Hz, 2H), 3.99-3.82 (m, 6H), 3.40 (s, 3H), 2.48 (t, J=6.3 Hz, 4H), 2.13 (br s, 3H), 1.86-1.70 (m, 6H), 1.63 (s, 12H), 1.00 (t, J=7.4 Hz, 6H); $^{13}$C NMR (100 MHz, CD$_3$CN) δ 175.3, 171.4, 170.7, 144.1, 143.4, 141.6, 129.3, 125.0, 124.4, 123.1, 110.8, 97.3, 63.5, 57.6, 49.1, 45.9, 45.7, 29.3, 25.5, 22.8, 21.2, 21.0, 11.7. IR (thin film) 1735, 1543, 1503, 1341, 1249 cm$^{-1}$; HRMS (ESI) calculated for $C_{41}H_{54}N_3O_2$ (M$^+$) 620.4211, observed 620.4185.

This example demonstrated that, consistent with a requirement for initial N-activation, different acylation conditions produced divergent reaction pathways. Unlike the peptide coupling conditions used to produce compound 11, a combination of acetyl chloride and a weak base, 2,6-lutidine, provided only O-acylation product 17 in high yield.

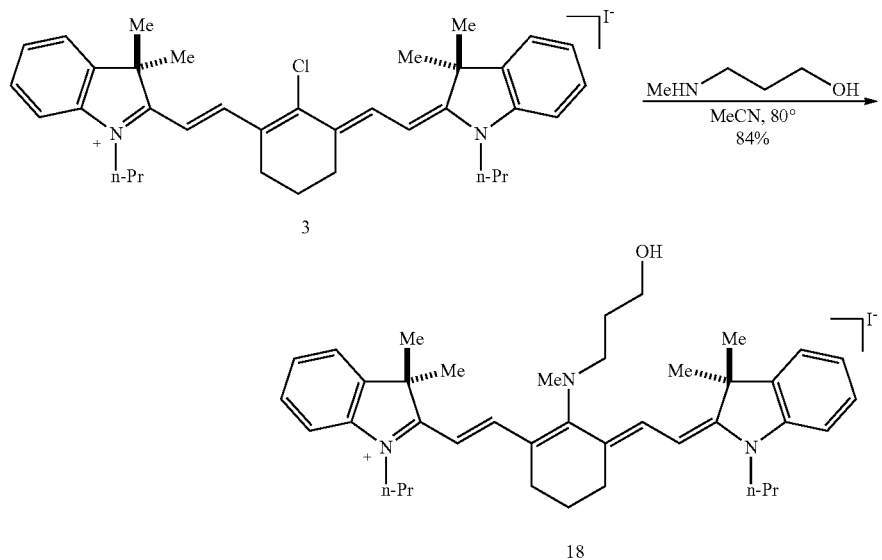

(17): To a mixture of 6 (30 mg, 0.043 mmol) and 2,6-lutidine (20 μL, 0.17 mmol) in DCM (1 mL) was added acetyl chloride (9.0 μL, 0.13 mmol). The blue solution was stirred for 16 hours at room temperature, at which time (18): To a solution of IR-780 iodide 3 (315 mg, 0.472 mmol) in MeCN (3 mL) was added 3-methylamino-1-propanol (230 μL, 2.36 mmol). The solution was heated to 80° C. in a sealed vial for 10 minutes as the reaction color transitioned from green to dark blue. After this time LC/MS analysis showed complete consumption of 3. The reaction mixture was concentrated in vacuo, and the residue was purified by silica gel chromatography (0→10% MeOH/DCM) to afford 18 (285 mg, 84%) as a dark blue iridescent solid. $^1$H NMR (CD$_3$CN, 400 MHz) δ 7.51 (d, J=13.3 Hz, 2H), 7.38 (d, J=7.3 Hz, 2H), 7.33-7.25 (m, 2H), 7.13-7.03 (m, 4H), 5.83 (d, J=13.4 Hz, 2H), 3.86 (m, 6H), 3.55 (q, J=5.6 Hz, 2H), 3.40 (s, 3H), 3.02 (t, J=4.9 Hz, 1H), 2.47 (t, J=6.6 Hz, 4H), 2.01-1.93 (m, 2H), 1.83-1.69 (m, 6H), 1.59 (s, 12H), 0.98 (t, J=7.4 Hz, 6H); $^{13}$C NMR (CD$_3$CN, 125 MHz) δ 176.8, 169.4, 144.2, 142.2, 141.3, 129.1, 124.3, 123.8, 122.9, 110.3, 95.9, 59.6, 56.8, 48.6, 45.7, 45.4, 32.5, 29.4, 25.4, 22.6, 20.8, 11.6; IR (thin film) 3339, 1540, 1508, 1449, 1344, 1256 cm$^{-1}$; HRMS (ESI) calculated for C$_{40}$H$_{54}$N$_3$O (M$^+$) 592.4261, observed 592.4255.

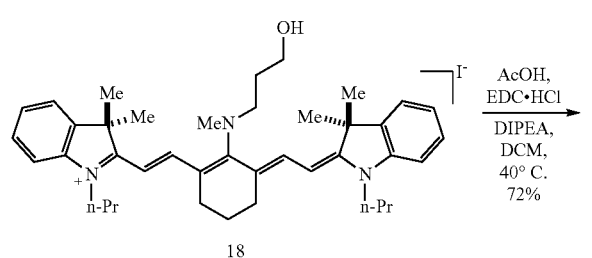

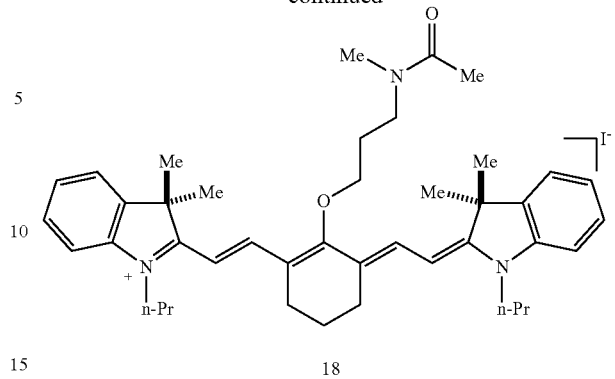

(19): To a solution of alcohol 18 (25 mg, 0.035 mmol), acetic acid (8 μL, 0.14 mmol), and DIPEA (6 μL, 0.035 mmol) in DCM (2 mL) was added EDC.HCl (27 mg, 0.14 mmol) at room temperature. The vial was sealed and the reaction was heated to 40° C. for 48 hours. After this time LC/MS analysis showed complete consumption of 18. The reaction was diluted with saturated aqueous sodium iodide (10 mL), extracted with dichloromethane (2×10 mL), and dried over Na$_2$SO$_4$. The solvent removed in vacuo, and the green residue was purified by silica gel chromatography (0→10% MeOH/DCM) affording 19 mg (72%) of 19 as an iridescent green solid. $^1$H NMR (400 MHz, CD$_3$CN, 72° C.; compound exists as a mixture of rotamers, major rotamer is designated by *, minor rotamer denoted by §)δ 8.11 (d, J=14.2 Hz, 2H), 7.49-7.45 (m, 2H), 7.42-7.37 (m, 2H), 7.27-7.20 (m, 4H), 6.10 (d, J=14.2 Hz, 2H), 4.13-3.98 (m, 6H), 3.68-3.51 (m, 2H), 3.04 (br s, 3H*), 2.94 (br s, 3H$^§$), 2.61 (t, J=6.2 Hz, 4H), 2.31-2.17 (m, 2H), 2.07 (br s, 3H$^§$), 2.00 (br s, 3H*), 1.91-1.80 (m, 6H), 1.70 (s, 12H), 1.03 (t, J=7.4 Hz, 6H). IR (thin film) 1632, 1551, 1505, 1393, 1360, 1245 cm$^{-1}$; HRMS (ESI) calculated for C$_{42}$H$_{56}$N$_3$O$_2$ (M$^+$) 634.4367, observed 634.4355.

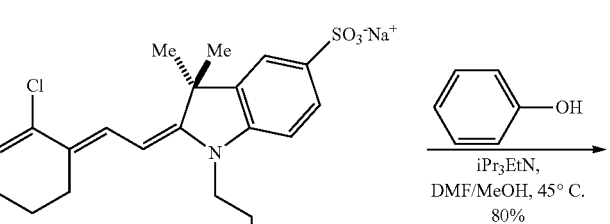

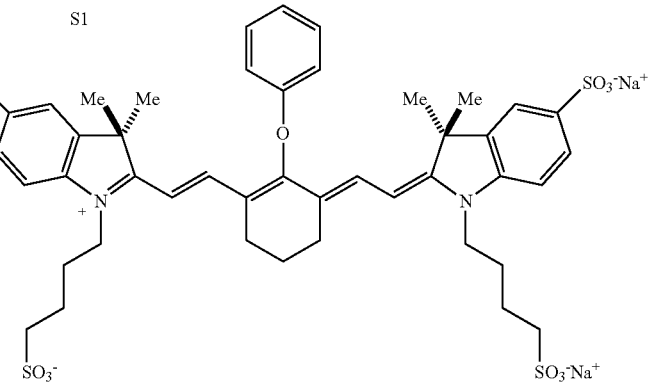

(21): 21 was prepared according to procedure of Strekowski et. al. (*J. Org. Chem.* 1992, 57, 4578-4580). To a solution of S1 (38 mg, 0.040 mmol) in DMF (0.7 mL) and MeOH (0.7 mL) was added phenol (26 mg, 0.28 mmol) and diisopropylethylamine (48 μL, 0.28 mmol). The dark green solution was heated to 45° C. in a sealed vial for 3 hours, after which time LC/MS analysis showed complete consumption of S1. The reaction was cooled to room temperature and precipitated into $Et_2O$ (40 mL). The slurry was centrifuged, the supernatant discarded, and the green pellet was resuspended in $Et_2O$ (20 mL). The procedure was repeated, and the crude material was dissolved in 5 mL of water for an ion exchange step. A pipet was filled with 1.5 g of Dowex 50 W X8 strongly acidic 200-400 mesh resin, washed with 3 mL of water, 5 mL of 1M $H_2SO_4$, and finally 3 mL of water. The aqueous solution of the crude 21 was eluted (fast dropwise rate) through the Dowex column into an aqueous $NaHCO_3$ solution (70 mg in 2 mL water). After stirring for 5 minutes, this aqueous solution was loaded directly onto a $C_{18}Aq$ column and purified by reversed-phase chromatography (0→25% MeCN/water) to afford 21 (32 mg, 80%) as a dark green solid. $^1$H NMR ($CD_3OD$, 400 MHz) δ 8.02 (d, J=14.2 Hz, 2H), 7.85 (dd, J=8.3, 1.7 Hz, 2H), 7.78 (d, J=1.7 Hz, 2H), 7.47-7.37 (m, 2H), 7.34 (d, J=8.3 Hz, 2H), 7.14 (d, J=8.7 Hz, 2H), 7.06 (t, J=7.6 Hz, 1H), 6.26 (d, J=14.2 Hz, 2H), 4.28-4.05 (m, 4H), 2.89 (t, J=6.8 Hz, 4H), 2.82-2.75 (m, 4H), 2.11-2.01 (m, 2H), 2.01-1.87 (m, 8H), 1.37 (s, 12H); $^{13}$C NMR ($CD_3OD$, 100 MHz) δ 174.0, 165.9, 161.3, 144.9, 143.8, 143.1, 142.3, 131.5, 128.1, 124.6, 123.7, 121.2, 115.8, 111.6, 101.9, 51.7, 50.2, 45.0, 28.1, 27.1, 25.2, 23.5, 22.4; IR (thin film) 1558, 1512, 1431, 1400, 1361 $cm^{-1}$; HRMS (ESI) calculated for $C_{44}H_{49}N_2O_{13}S_4$; (M-3H$^{-3}$) 313.7367, observed 313.7361.

(22): 22 was prepared according to procedure of Strekowski et. al. (*J. Org. Chem.* 1992, 57, 4578-4580). To a solution of S1 (35 mg, 0.037 mmol) in DMF (2 mL) and MeOH (50 μL) was added β-mercaptoethanol (10 μL, 0.15 mmol) and diisopropylethylamine (26 μL, 0.15 mmol). The dark green solution was heated to 35° C. in a sealed vial for 4 hours. The reaction was cooled to room temperature and precipitated into $Et_2O$ (40 mL). The slurry was centrifuged, the supernatant discarded, and the green pellet was resuspended in $Et_2O$ (20 mL). The procedure was repeated, and the crude material was dissolved in 5 mL of water for an ion exchange step. A pipet was filled with 1.5 g of Dowex 50 W X8 strongly acidic 200-400 mesh resin, washed with 3 mL of water, 5 mL of 1M $H_2SO_4$, and finally 3 mL of water. The aqueous solution of the crude 22 was eluted (fast dropwise rate) through the Dowex column into an aqueous $NaHCO_3$ solution (70 mg in 2 mL water). After stirring for 5 minutes, this aqueous solution was loaded directly onto a $C_{18}Aq$ column and purified by reversed-phase chromatography (0→20% MeCN/water) to afford 22 (23 mg, 64%) as a dark green solid. $^1$H NMR (DMSO-$d_6$, 500 MHz) δ 8.77 (d, J=14.1 Hz, 2H), 7.77 (d, J=1.6 Hz, 2H), 7.65 (dd, J=8.3, 1.6 Hz, 2H), 7.38 (d, J=8.3 Hz, 2H), 6.36 (d, J=14.1 Hz, 2H), 4.96 (t, J=5.3 Hz, 1H), 4.28-4.11 (m, 4H), 3.50 (q, J=6.3 Hz, 2H), 2.87 (t, J=6.7 Hz, 2H), 2.71-2.61 (m, 4H), 2.56-2.51(m, 4H), 1.89-1.72 (m, 10H), 1.70 (s, 12H); $^{13}$C NMR (DMSO-$d_6$, 125 MHz) δ 171.9, 155.2, 145.0, 145.0, 142.2, 140.3, 133.4, 126.2, 119.8, 110.4, 101.7, 60.1, 50.7, 48.8, 43.7, 39.1 (observed by HSQC correlation), 27.4, 26.0, 25.7, 22.5, 20.7; IR (thin film) 3410, 1530, 1507, 1432, 1348, 1248 $cm^{-1}$; HRMS (ESI) calculated for $C_{40}H_{49}N_2O_{13}S_5$; (M-3H$^{-3}$) 308.3941, observed 308.3937.

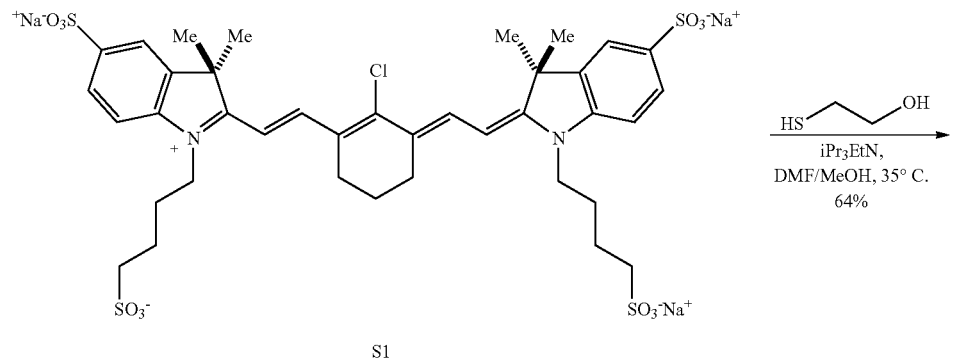

S1

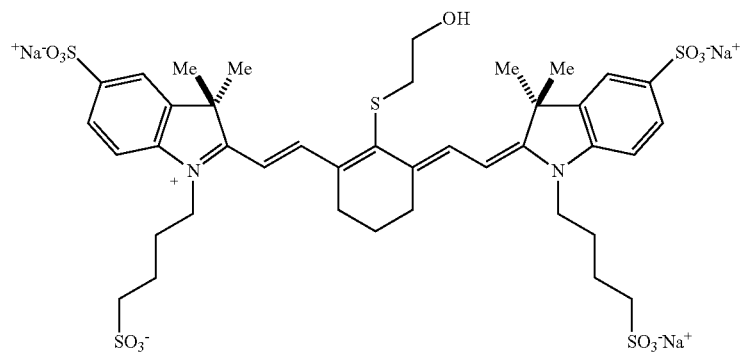

22

Example 2

Kinetic Effect of Alkanolamine Chain Length on Rearrangement

The rearrangement kinetics of the N-ethanolamine substituted compound 6 and its N-propanolamine homolog 18 were compared.

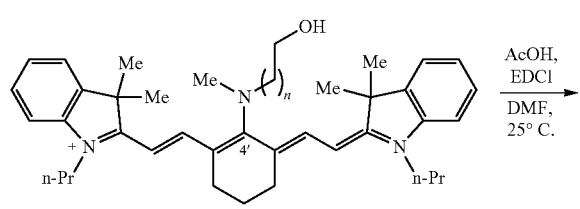

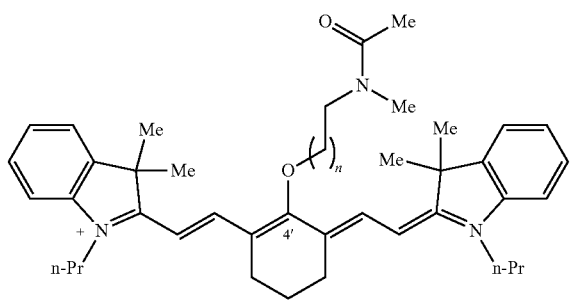

6, n = 1
6 to 11: $t_{1/2}$ = 37 min
11, n = 1
18, n = 2
18 to 19: $t_{1/2}$ = 720 min
19, n = 2

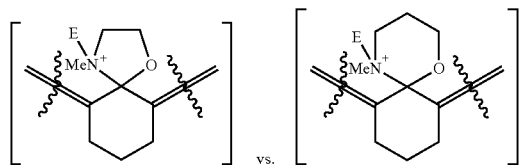

Figure 2A:
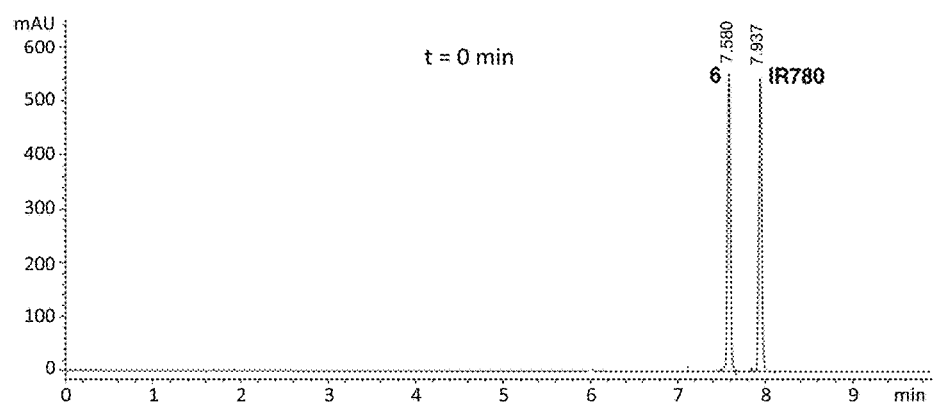
FIGS. 2A and 2B are chromatograms of an N-ethanolamine substituted compound at 0 minutes (FIG. 2A) and its corresponding C4'-alkyl-ether heptamethine cyanine fluorophore formed via rearrangement after a reaction time of 300 minutes (FIG. 2B); the chromatograms were obtained at 700 nm, and an internal standard was included.
Figure 2B:
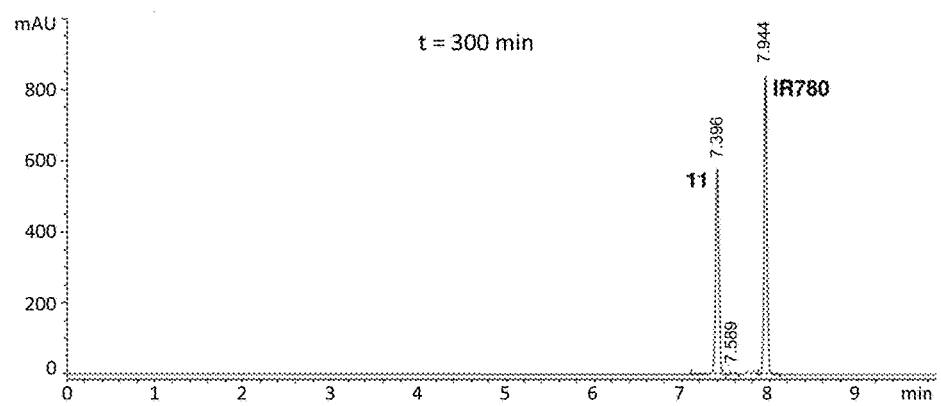
Figure 3A:
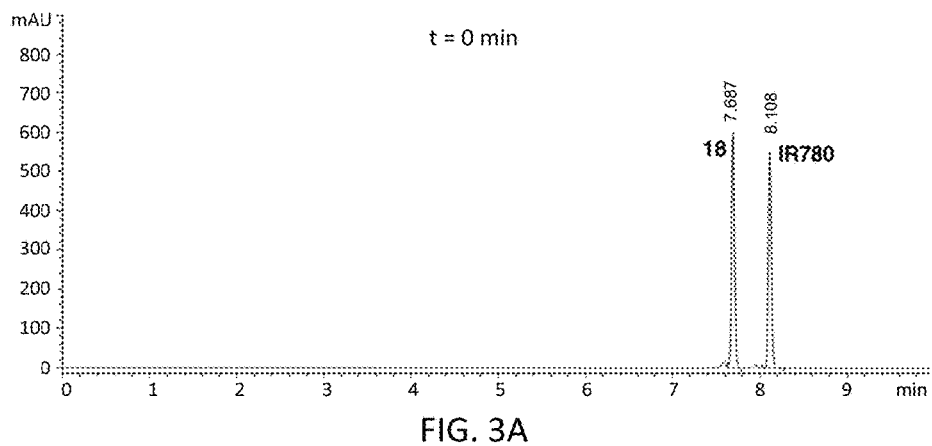
FIGS. 3A and 3B are chromatograms of an N-propanolamine substituted compound at 0 minutes (FIG. 3A) and its corresponding C4'-alkyl-ether heptamethine cyanine fluorophore formed via rearrangement after a reaction time of 2400 minutes (FIG. 3B); the chromatograms were obtained at 700 nm, and an internal standard was included.
Figure 3B:
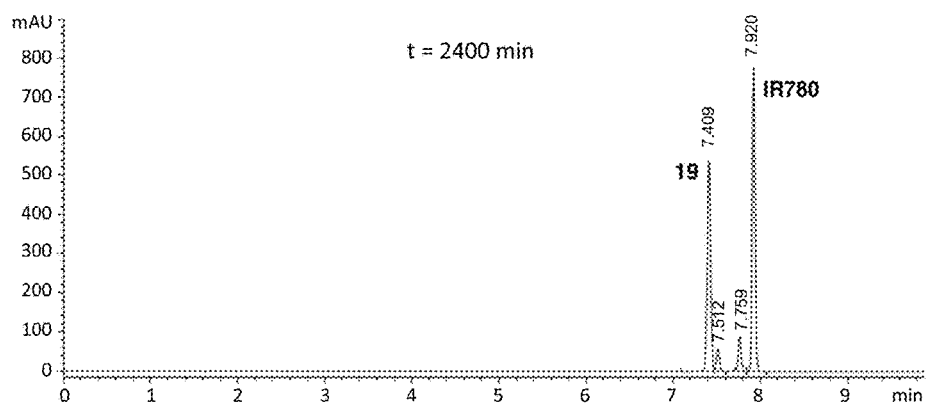

To a solution of alcohol 6 or 18 (0.015 mmol), acetic acid (0.060 mmol), and DIPEA (0.015 mmol) in DCM (0.5 mL) was added an internal standard (IR-780, 0.015 mmol). A t=0 min, a sample was withdrawn and analyzed by HPLC. EDC.HCl (0.060 mmol) was added and the reaction was heated to 35° C. At the given time points in FIG. 2 (compound 6 to 11) and FIG. 3 (compound 18 to 19), a 5 μL aliquot was withdrawn and diluted in 500 μL methanol (to halt the reaction progress). The sample was then analyzed on an Agilent 1260 Infinity HPLC utilizing a Kinetex 5 μm C6-Phenyl 110 Å (4.6×250 mm) column (Phenomenex Inc.) with a gradient of 5→98% (10 min) to 98→5% (1 min) MeCN/0.1% aqueous trifluoroacetic acid at a flow rate of 2.0 mL/min. Experiments were run in duplicate and plotted with error bars derived from the standard deviation (<5% in all cases). The peaks were assigned by comparing retention times with purified standards.

While 6 reacted relatively rapidly ($t_{1/2}$=37 min) to form 11, 18 proceeded much more slowly ($t_{1/2}$=720 min), though ultimately in good conversion to 19, and with satisfactory isolated yield (72%) (FIG. 4). The kinetic dependence on ring size (5-membered faster than 6-membered) suggested that acyl-ammonium formation, which is likely reversible, precedes rate determining, and presumably, irreversible tetrahedral intermediate formation.

Without wishing to be bound by a particular theory of operation, it is thought that the rearrangement proceeds through tetrahedral intermediates. However, concerted displacement or hemolysis/recombination pathways cannot be completely excluded.

Example 3

Reversibility of the Rearrangement

The reversibility of the rearrangement was examined.

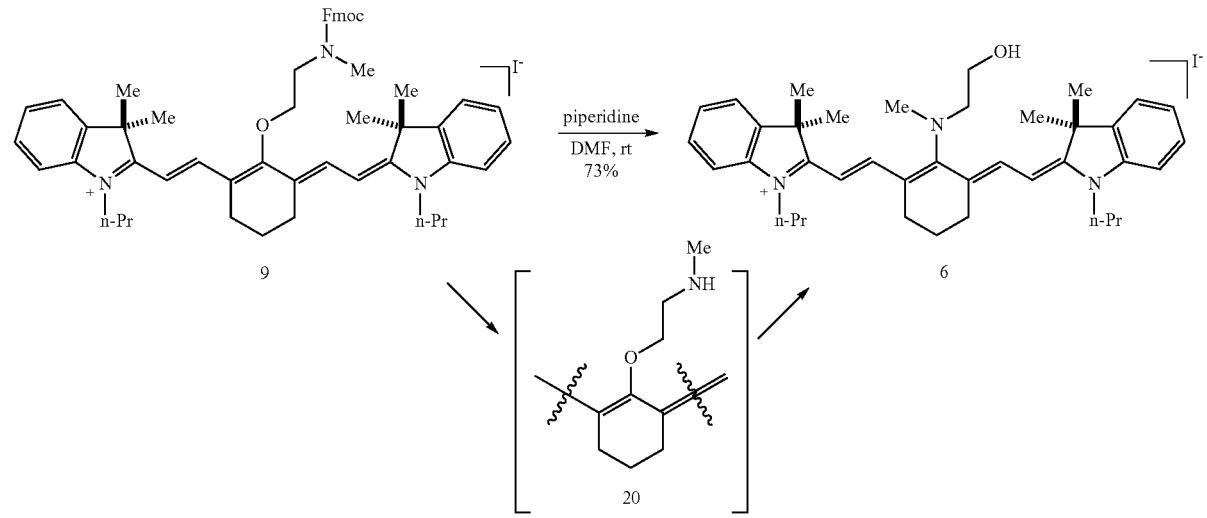

When Fmoc-protected 9 was exposed to piperidine in DMF, the C4'-N-methylethanolamine-substituted product 6, its synthetic precursor, was rapidly generated. To a solution of 9 (18 mg, 0.019 mmol) in DMF (300 μL) was added piperidine (10 μL, 0.097 mmol). The green solution was stirred at room temperature for 20 minutes, during which time the reaction color transitioned to dark blue and a precipitate resulted. At this time LC/MS analysis showed a complete conversion of 9 to 6. The reaction mixture was diluted with DCM (20 mL), washed with water (4×5 mL), saturated aqueous sodium iodide (2×5 mL), and dried over $Na_2SO_4$. The volatiles were concentrated in vacuo, and the blue residue was purified by silica gel chromatography (50% EtOAc/DCM, 0→25% MeOH/DCM) affording 10 mg (73%) of product. The analytical data were consistent with those for compound 6.

Without wishing to be bound by any particular theory of operation, this process likely occurred through the intermediacy of O-linked species 20. This observation suggests a thermodynamic preference for C4'-N-linkage. The facile conversion of 9 to 6 altered the absorbance maxima by almost 90 nm, suggesting potential for various optical sensing applications.

Example 4

Determination of Quantum Yields and Molar Absorption Coefficients

Quantum yields ($\Phi_f$) were determined in methanol relative to ICG and IR783 ($\Phi_f$=0.078 and 0.084, respectively; James et al., *Theranostics* 2013, 3, 692-702), from plots of integrated fluorescence intensity vs. absorbance, according to the following relationship:

$$\Phi_x = \Phi_{st}\left(\frac{Grad_x}{Grad_{st}}\right)\left(\frac{\eta_x}{\eta_{st}}\right)$$

where subscripts st and x denote standard and test sample, respectively, $\Phi$ is the fluorescence quantum yield, Grad is the gradient of the integrated fluorescence intensity vs. absorbance plot, and η is the refractive index of the solvent (Parker, et al., *Analyst* 1960, 85, 587; Williams, et al., *Analyst*. 1983, 108, 1067; Rurack, et al., *Anal. Chem.* 2011, 83, 1232; Samanta, et al., *Chem. Commun.* 2010, 46, 7406). Measurements were performed in 10 mm path length quartz cuvettes (Hellma 111-QS), maintained at 25° C., with the absorbance of all dye solutions ≤0.08 in order to maximize illumination homogeneity and optical transparency and minimize reabsorption effects (Samanta, et al., *Chem. Commun.* 2010, 46, 7406). ICG and IR783 standards and test dye solutions were excited at 70 nm below their absorbance maxima.

Molar absorption coefficients (ε) were determined in PBS using Beer's law, from plots of absorbance vs. concentration. Measurements were performed in 10 mm path length quartz cuvettes (Hellma 111-QS), maintained at 25° C., with absorbance at the highest concentration≤0.08 (see above).

Figure 5A:
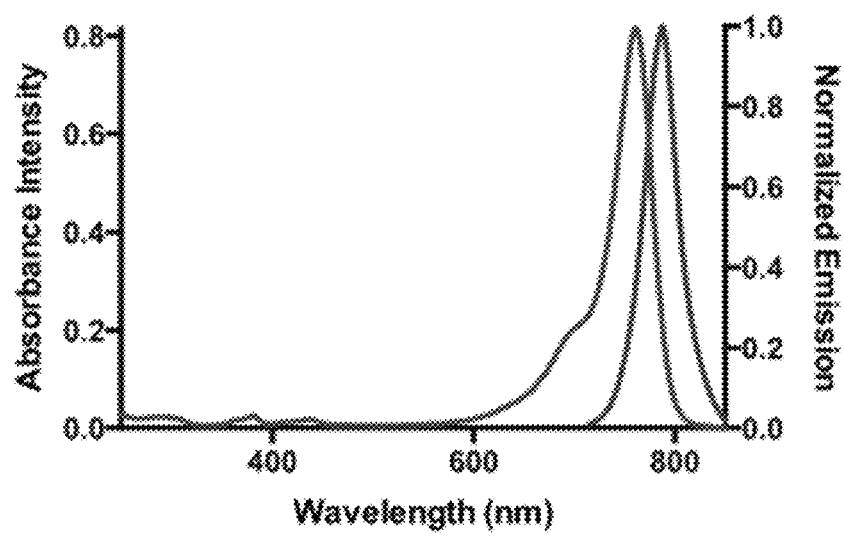
FIGS. 5A and 5B are absorbance and normalized emission spectra of two exemplary C4'-alkyl-ether heptamethine cyanine fluorophores.
Figure 5B:
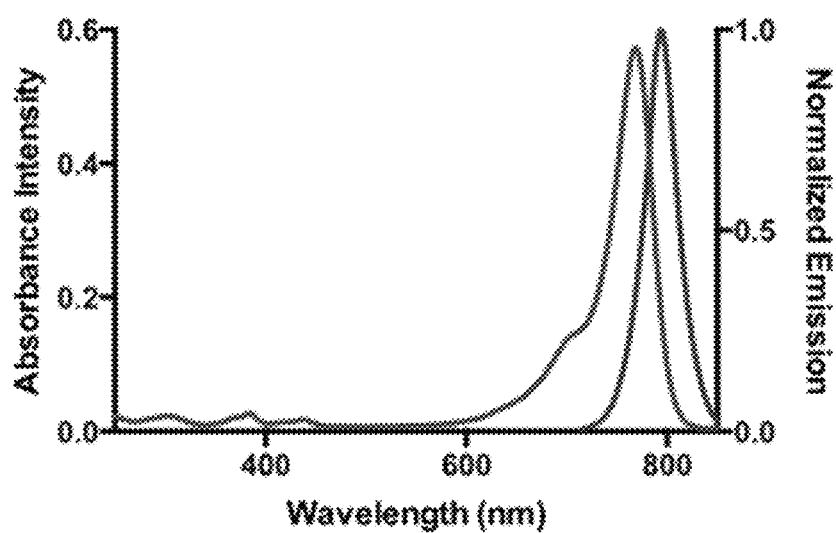

Representative compounds 8 (5 μM in methanol) and 13 (3 μM in methanol) were found to possess similar absorbance and normalized emission spectra (FIGS. 5A and 5B, respectively) and improved quantum yield relative to a standard heptamethine cyanine, indocyanine green (ICG) (Table 4).

TABLE 4

| Compound | $\lambda_{max}$ (nm) | $\lambda_{em}$ (nm) | ε ($M^{-1}cm^{-1}$) | $\Phi_f$ |
|---|---|---|---|---|
| ICG | 785 | 822 | 204,000 | 0.078 |
| 8[a] | 774 | 797 | 187,000 | 0.22 |
| 13[a] | 774 | 798 | 214,000 | 0.23 |

[a]Measured in methanol relative to ICG.

Example 5

Stability of C4'-Alkyl-Ether Heptamethine Cyanine Fluorophores

The thiol reactivity of 13 was compared with phenol-substituted 21 and S-mercaptoethanol-substituted 22.

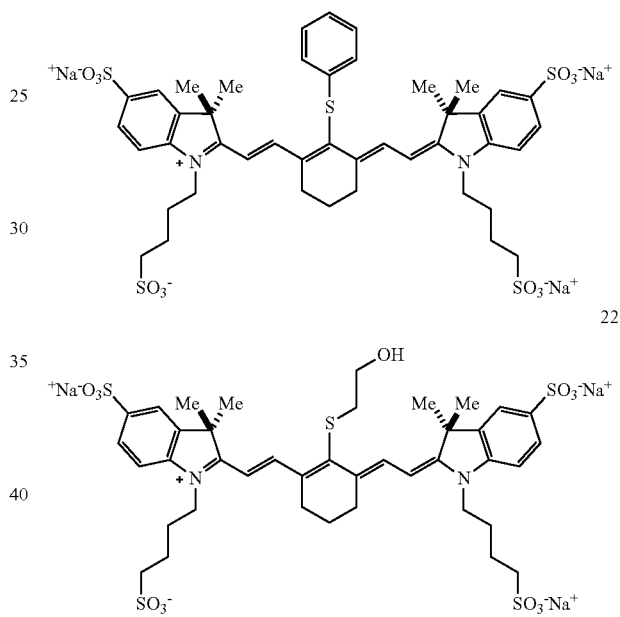

Stock solutions (5 mM) of 13, 21, and 22 were prepared in DMSO. A five hundred-fold dilution in 50 mM PBS buffer (pH=7.4) was performed to yield 10 μM samples. The samples were analyzed by HPLC (t=0 min) and 5 μL of a 0.2 M glutathione solution in deionized water was added to afford a 1 mM final glutathione concentration. The samples were continuously analyzed every 20 minutes by HPLC, and the integrated peak areas of absorbance at 780 nm from the starting dyes were plotted versus time. The samples were analyzed on an Agilent 1260 Infinity HPLC utilizing a Kinetex 5 μm Biphenyl 100 Å (4.6×250 mm) column (Phenomenex Inc.) with a gradient of 2→98% (4.7 min) to 98→2% (1 min) MeCN/10 mM ammonium carbonate at a flow rate of 1.5 mL/min. Experiments were run in duplicate and plotted with error bars derived from the standard deviation (<5% in all cases). After the reaction of 21 and GSH achieved full conversion the reaction was directly purified by semi-prep HPLC to obtain glutathione-cyanine adduct 23, which was analyzed by HRMS. HRMS (ESI) calculated for $C_{48}H_{60}N_5O_{18}S_5$; $(M-3H^{-3})$ 384.7507, observed 384.7500.

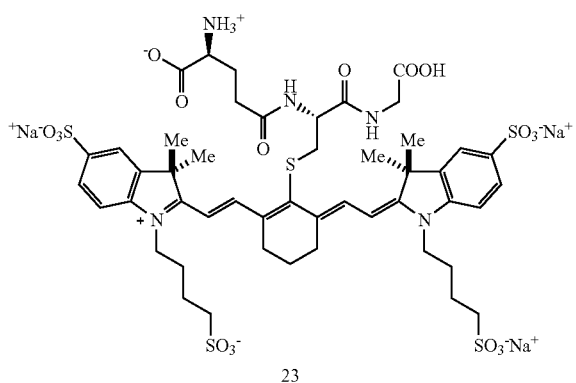

23

Figure 6:
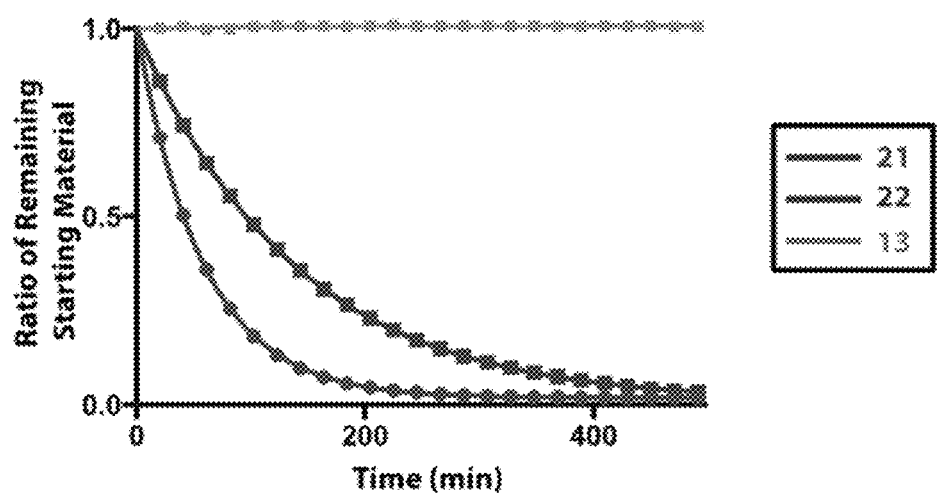
FIG. 6 illustrates the relative stability of an exemplary C4'-alkyl-ether heptamethine cyanine fluorophore compared to C4' phenol- and thiol-substituted heptamethine cyanines in the presence of thiol nucleophiles.

With compounds 21 and 22, rapid conversion to the glutathione adduct 23 was observed ($t_{1/2}$=95 and 40 minutes, respectively), as shown in FIG. 6. By contrast, the alkyl-ether 13 showed no decomposition over the same time period and >90% was present after 3 days.

Without wishing to be bound by any particular theory of operation, the dramatic differences in reactivity are thought to stem from the significantly different energetic requirements involved in ionizing phenolate, thiolate, and alkoxide leaving groups. This study clearly demonstrates the superior chemical stability of these new C4'-alkyl ethers over conventional phenol or thiol-substituted heptamethine cyanines.

Figure 7:
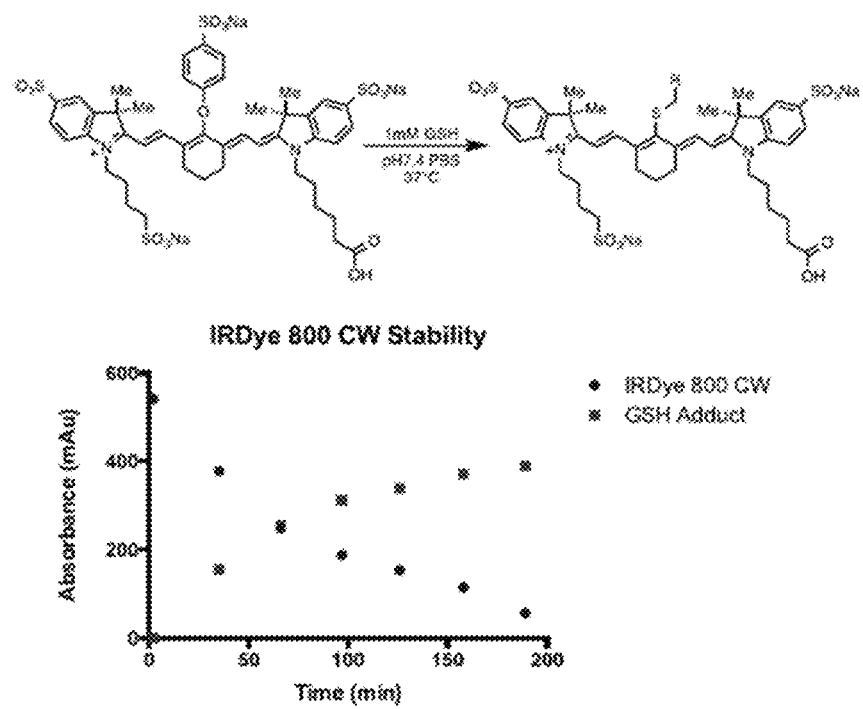
FIG. 7 illustrates the reaction between glutathione and a commercially available heptamethine cyanine fluorophore and shows the formation of the glutathione adduct over time.
Figure 8:
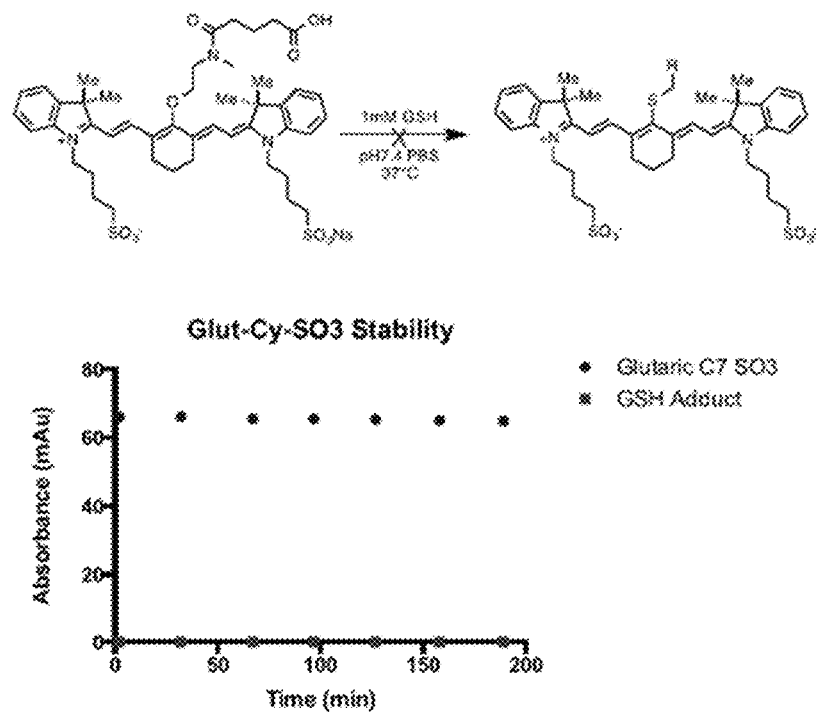
FIG. 8 illustrates the absence of a reaction between glutathione and an exemplary C4'-alkyl-ether heptamethine cyanine fluorophore.

Solutions of commercially available IRDye 800 CW (a phenol-substituted heptamethine cyanine available from Li-Cor Biotechnology, Lincoln, Nebr.) and compound 13 (Glut-Cy-SO3), 10 μM, were prepared in pH 7.4 phosphate-buffered saline and exposed to physiologically relevant concentrations of glutathione (GSH, 1 mM) at room temperature. Whereas the phenol-based fluorophore degraded within 3 hours to provide the glutathione (—S—R) adduct ($t_{1/2}$=50 minutes, FIG. 7, measured by HPLC area under curve), the C4'-alkyl-ether Cy7 compound 13 showed minimal decomposition over the same time period and was stable for >2 days (FIG. 8). Upon analysis by LCMS, signals consistent with the glutathione adduct were observed concomitant with the disappearance of the phenol (IRDye 800 CW) (FIG. 7). In contrast, no formation of the glutathione adduct was observed with compound 13.

Example 6

Antibody Labeling

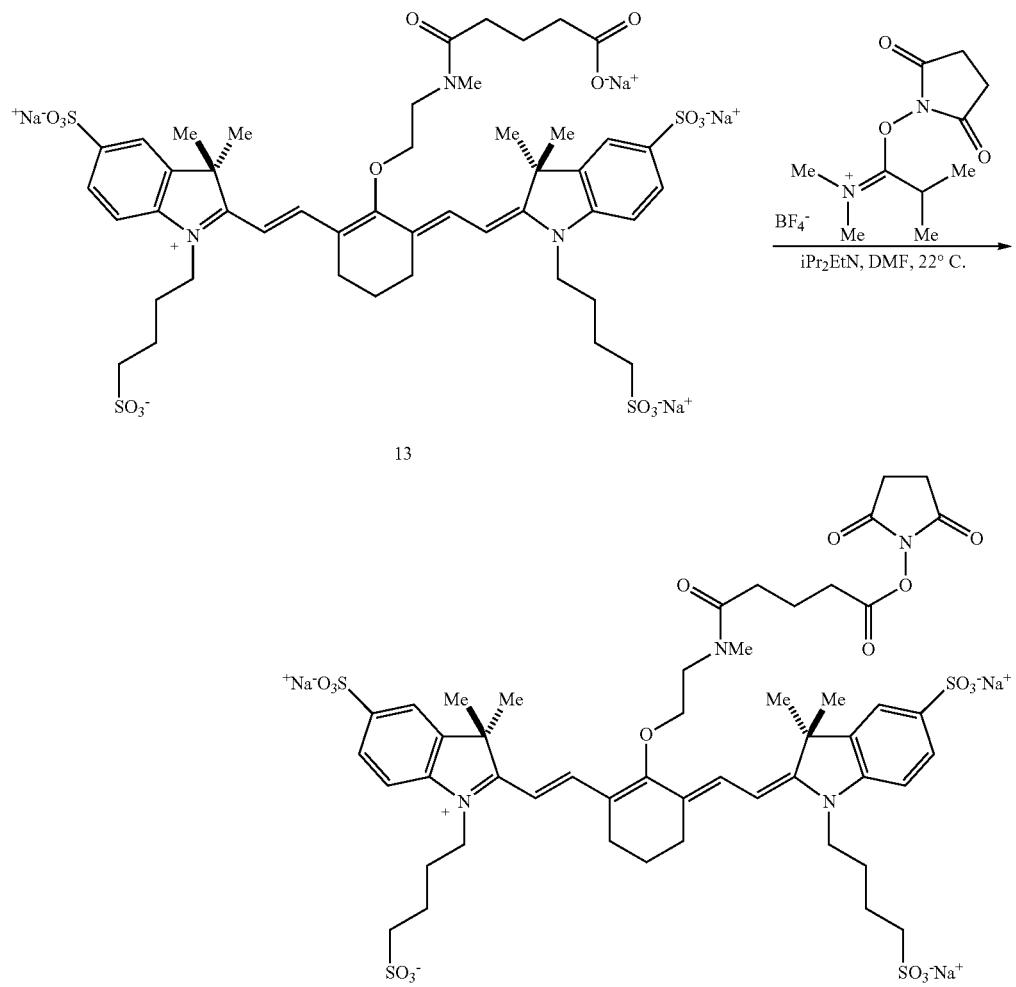

NHS ester synthesis: A suspension of 13 (14 mg, 0.012 mmol) in toluene (5 mL) was concentrated in vacuo to azeotropically remove water. A solution of TSTU (N,N,N', N'-tetramethyl-O—(N-succinimidyl)uranium tetrafluoroborate, 7.5 mg, 0.025 mmol) and diisopropylethylamine (2.2 µL, 0.012 mmol, 1 equivalent) in DMF (500 µL) was added to 13 under an argon atmosphere. This solution was heated to 35° C. for 16 hours. After this time LC/MS analysis showed complete consumption of 13. The reaction was subsequently precipitated into ethyl acetate (45 mL), centrifuged, and the supernatant decanted off. The green pellet was resuspended in $Et_2O$ (20 mL), and the centrifugation procedure was repeated twice. The crude solid (S2) was placed under vacuum (<0.5 Torr) for 1 hour and used directly in the antibody conjugation step.

Figure 9:
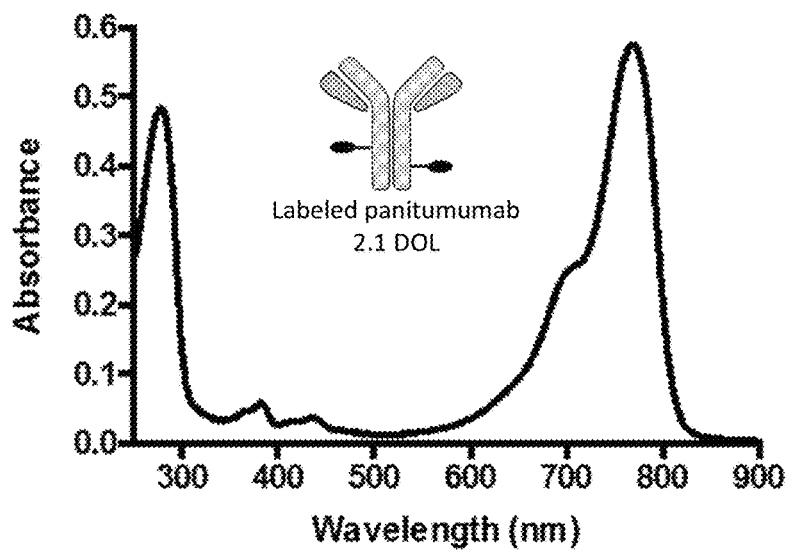
FIG. 9 is an absorbance spectrum of panitumumab conjugated to an exemplary C4'-alkyl-ether heptamethine cyanine fluorophore.

Panitumumab conjugation (Bhattacharyya et al., *Med Chem. Comm.* 2014, 5, 1337-1346): To 500 µL of 1M PBS (pH 8.5) in a 1.5 mL microcentrifuge tube was added 500 µL of panitumumab solution, a 5 mg/mL solution acquired from Amgen, and 38 µL of a 5 mM DMSO solution of S2 under subdued lighting. The microcentrifuge tube was gently inverted twice to mix the solution and placed in a dark box on a slowly rocking platform for one hour at room temperature. A G10 Sephadex column acquired from GE Healthcare was primed with six column volumes of 0.9% saline. After one hour on the rocking platform, the solution was eluted through the column with 0.9% saline and collected in a 2 mL Cryotube. 1 mL was collected per fraction. The dye and antibody concentrations were determined by UV-Vis spectroscopy using Beer-Lambert's Law $C=A/\varepsilon l$ with the extinction coefficient of 168,000 $M^{-1}cm^{-1}$ at 774 nm in 1M PBS and 200,000 $M^{-1}cm^{-1}$ at 280 nm 1:1 PBS:MeOH for 13 and panitumumab, respectively. The degree of labeling (DOL), the average number of dye molecules (compound 13) bonded to one antibody, was determined as the quotient of dye concentration and antibody concentration. A DOL of 2.1-2.2 was obtained. The solution of antibody-conjugate was then filtered through a 0.22 µm sterile filter acquired from Acrodisc for storage at 4° C. A UV-Vis-NIR absorbance spectrum of the panitumumab-13 conjugate is shown in FIG. 9.

Cell culture: DA-MB-468 (EGFR/HER1 overexpression; Rae et al., *Breast Cancer Res. Treat* 2004, 87, 87-95; Mamot et al., *Cancer Res.* 2003, 63, 3154-3161) and MCF7 (normal EGFR/HER1 expression; Williams et al., *Analyst* 1983, 108, 1067-1071) human breast cancer cell lines were obtained from the National Cancer Institute Developmental Therapeutics Program, DCTD Tumor Repository. MDA-MB-468 was cultured in RPMI supplemented with 2 mM L-glutamine, 11 mM D-glucose, 24 mM sodium bicarbonate, 10% heat-inactivated fetal bovine serum, 100 units/mL penicillin, 100 µg/mL streptomycin, and 0.25 µg/mL amphotericin B. MCF7 was cultured in DMEM supplemented with 4 mM L-glutamine, 25 mM D-glucose, 44 mM sodium bicarbonate, 10% heat-inactivated fetal bovine serum, 100 units/mL penicillin, 100 µg/mL streptomycin, and 0.25 µg/mL amphotericin B. Both cell lines were grown at 37° C. in an atmosphere of 20% $O_2$ and 5% $CO_2$. Stock cultures were maintained in continuously exponential growth by weekly passage of the appropriate number of cells following trypsinization with 0.25% Trypsin-EDTA (0.9 mM) in PBS.

Fluorescence microscopy: MDA-MB-468 or MCF7 cells ($1\times10^5$) were plated on Nunc Lab-Tek® II chambered #1.5 German borosilicate coverglass (Thermo Fisher Scientific, Inc.) and allowed to adhere overnight. Cells were incubated with 100 nM Panitumumab-13 for 2 h, washed twice with PBS, incubated with 1 µM Hoechst 33342 for 0.5 h, washed twice with PBS, and imaged. Fluorescence microscopy was performed using an Evos® FL Auto Imaging System (Life Technologies) at 40× magnification using a coverslip-corrected plan fluorite objective. Near-IR fluorescence was imaged using a Cy7 LED light cube (710/40 nm excitation, 775/46 nm emission) and Hoechst using a DAPI LED light cube (357/44 nm excitation, 447/60 nm emission). Image processing was conducted with ImageJ 1.49f.

Flow cytometry: MDA-MB-468 or MCF7 cells ($1\times10^6$) were seeded into 6-well plates and allowed to adhere overnight. Cells were incubated with 100 nM Panitumumab-13 for 2 h and washed twice with PBS. Flow cytometric analysis for near-IR fluorescence signal was performed at the CCR Flow Cytometry Core (NCI-Frederick) using a BD LSRII Fortessa analyzer operating a laser line at 647 nm. Data processing was conducted with FlowJo vX.0.7.

Figure 10:
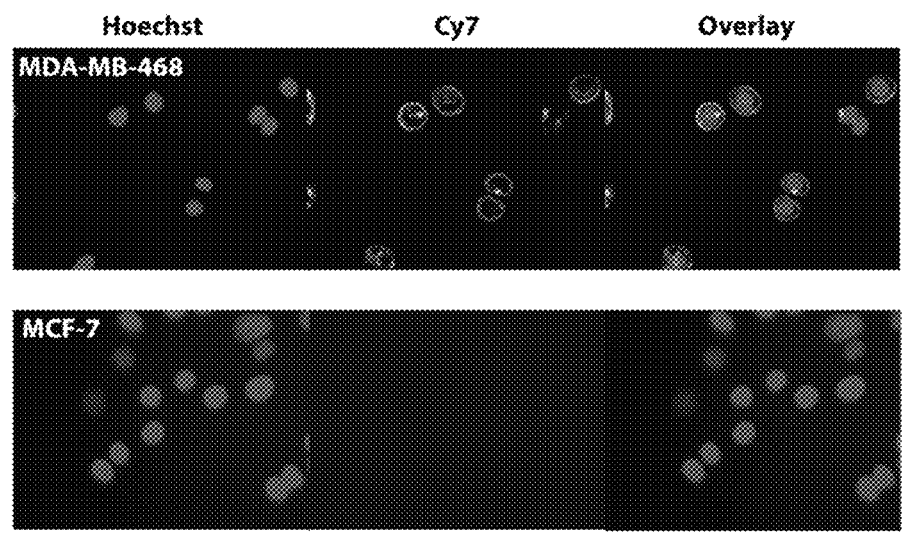
FIG. 10 is two fluorescence microscopy images of live MDA-MB-468 (HER1+) and MCF-7 (HER1−) cells treated with 100 nM labeled panitumumab and Hoechst 33342 (1 µM).
Figure 11:
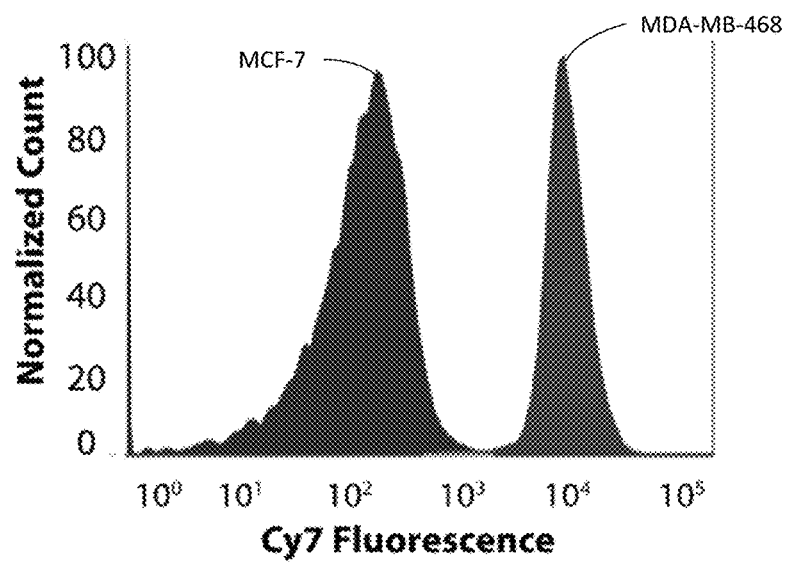
FIG. 11 provides flow cytometry results of MDA-MB-468 and MCF-7 cells treated with 100 nM labeled panitumumab.

Localization characteristic of the labeled antibody was only observed in HER1+ cells by fluorescence microscopy using a standard Cy7 filter set ($\lambda_{ex}$=710 nm, $\lambda_{em}$=775 nm, FIG. 10). The efficient cellular labeling of the fluorophore-antibody conjugate was also confirmed using fluorescence-activated cell sorting (FACS) (FIG. 11). These results indicated that 13 and other fluorophores disclosed herein are likely to be suitable for a range of near-IR fluorescence applications.

Example 7

Folate Labeling

Compound 13 was converted to its NHS-ester (TSTU, DMF, 35° C.) as described in Example 6, and then reacted with folate-EDA (N-(2-aminoethyl) folic acid) to provide a folate conjugate. The conjugate was incubated with HeLa cells that were conditioned to overexpress the folate receptor. FIG. 12A is a fluorescence image of the cells stained with Hoechst 33342. FIG. 12B is a fluorescence image of the cells incubated with a conjugate of folate and an exemplary C4'-alkyl-ether heptamethine cyanine fluorophore (Folate-Cy7). FIG. 12C is a differential interference contrast (DIC) image of the cells. FIG. 12D is a merged image of the images in FIGS. 12B and 12C. Fluorescent staining was only observed in the cells treated with the compound 13-folate conjugate (FIGS. 12B, 12D). No fluorescence was seen when the cells were incubated with non-conjugated compound 13 (FIG. 12A).

Example 8

In Vivo Administration and Fluorescence-Guided Surgery

Embodiments of the disclosed C4'-alkyl-ether heptamethine cyanine fluorophores may be used for in vivo detection of target cells, such as cancer cells. In one example, a C4'-alkyl-ether heptamethine cyanine fluorophore, such as compound 13, is conjugated with an antibody capable of recognizing and binding to an antigen on a target cell. A suitable pharmaceutical composition comprising the fluorophore-antibody conjugate is administered to a subject having the target cells. For example, the pharmaceutical composition is injected into a subject with a tumor having an antigen to which the antibody is capable of binding. The subject may be a mouse with a xenograft. The tumor is irradiated with near-IR radiation and an image may be obtained. Fluorescence indicates presence of fluorophore-antibody conjugate bound to tumor cells. The tumor may be excised using the detected fluorescence for guidance. Sufficient tissue is excised to provide non-fluorescent margins surrounding the excision, indicating that the entire tumor has been removed.

Example 9

Cell Identification in a Tissue Sample

A C4'-alkyl-ether heptamethine cyanine fluorophore is coupled with an antibody capable of directly or indirectly recognizing and binding to an antigen on a target cell. Indirect recognition and binding is performed by first binding an anti-antigen antibody (e.g., a monoclonal antibody) to the antigen, and subsequently adding a fluorophore-antibody conjugate where the conjugate comprises an anti-antibody antibody (e.g., a polyclonal antibody). A tissue sample is incubated with the fluorophore-antibody conjugate under conditions sufficient to provide binding of the antibody if the antigen is present. Excess, unbound fluorophore-antibody conjugate is washed off the tissue sample. The tissue sample is irradiated with near-infrared radiation and viewed under conditions sufficient to visualize fluorescence emitted by the fluorophore. Fluorescence indicates presence of the antigen on the target cell.

Example 10

Drug Imaging

A C4'-alkyl-ether heptamethine cyanine fluorophore comprises a drug of interest. The drug is injected into a subject at a desired location. Presence of the drug at the desired location is verified with near-IR fluorescence imaging. If the drug preferentially locates in a particular location or tissue type after injection, a period of time is allowed to elapse before performing near-IR fluorescence imaging of the expected location or tissue type to visualize the drug location. Excretion of the drug, e.g., through the subject's urine, may be monitored by monitoring fluorescence of the urine over time to detect excretion of the drug-containing fluorophore.

Example 11

In Vivo Imaging

The epidermal growth factor receptor (EGFR, HER1, c-ErbB-1) is a transmembrane glycoprotein that is a member of a subfamily of type I receptor tyrosine kinases including EGFR, HER2, HER3, and HER4. The EGFR is constitutively expressed in many normal epithelial tissues, including the skin and hair follicle. Expression of EGFR is also detected in many human cancers including those of the head and neck, colon, and rectum. Panitumumab binds specifically to the EGFR on both normal and tumor cells, and competitively inhibits the binding of ligands for epidermal growth factor (EGF). In vitro assays and in vivo animal studies have shown that binding of Panitumumab to the EGFR blocks phosphorylation and activation of receptor-associated kinases, resulting in inhibition of cell growth, induction of apoptosis, and decreased matrix metalloproteinase and vascular endothelial growth factor production. Overexpression of this oncogene is associated with poor prognosis and aggressive tumor attributes.

A conjugate of 13 and panitumumab will be investigated in in vivo optical imaging experiments in mouse models of cancer. Animal studies are an important step in evaluating embodiments of the disclosed C4'-alkyl-ether heptamethine cyanine fluorophores for beneficial properties that might enable ultimate clinical application.

Mice are the preferred species for tumor imaging, because murine cancer models most closely represent human cancers. Nude mice and cell lines (MDA-MB-231 (High-expressing), MDA-MB-468 (medium-expressing), and BT-474 (low-expressing)) will be obtained from approved sources.

Cells will be obtained from an approved source (tumor repository). Cell culturing, harvesting, and preparation will be performed. Subcutaneous injections of up to $1 \times 10^6$ cells in 100 µl of Hanks Balanced Salt Solution in both axillary regions will be performed. Fluorescence imaging will be initiated when the xenograft tumor reaches approximately 4-6 mm in diameter.

Imaging:
a) # of animals per group to provide statistically significant data: 5;
b) # groups per study: 6 (3 cell lines×3 imaging agents);
c) 20% additional to allow for tumor incorporation variability.

Appropriate animal model (3 xenograft tumor bearing animals)×6 animals per group×1 gender (female)×3 imaging agents: 54 animals.

Biodistribution (non-tumor bearing mice; Athymic nu/nu):
a) # of animals per time-point to provide statistically significant data: 5 animals per time-point;
b) # of time-points per study: 7;
c) # imaging agents: 3;
d) # gender: 1 (female).

Two animals per time-point×7 time-points×1 gender (female and male)×3 imaging agents: 42 mice.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound, or a pharmaceutically acceptable salt thereof, of formula I:

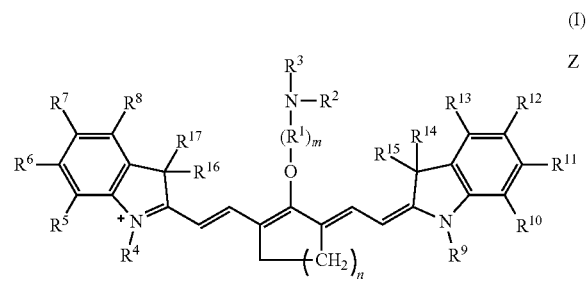

wherein m is 2, 3, 4, or 5;
n is 1, 2, or 3;
$R^1$ is —$CR^a_2$— where each $R^a$ independently is H, halo, optionally substituted alkyl, or optionally substituted aryl;
$R^2$ is optionally substituted alkyl, optionally substituted heteroalkyl, optionally substituted aryl, or optionally substituted heteroaryl;

R³ is a maleimidyl-containing group, a succinimidyl-containing group, optionally substituted alkoxy, optionally substituted alkyl carbonyl, optionally substituted alkoxy carbonyl, a drug, or a biomolecule-containing group;

R⁴ to R¹³ independently are H, optionally substituted alkyl, optionally substituted amino, or a sulfonate-containing group, wherein R⁶ and R⁷ optionally together form a substituted or unsubstituted cycloalkyl or aryl, and R¹² and R¹³ optionally together form a substituted or unsubstituted cycloalkyl or aryl;

R¹⁴ to R¹⁷ independently are alkyl; and

Z is a monatomic or polyatomic ion having a charge sufficient to provide a neutral compound.

2. The compound of claim 1, wherein R³ is a biomolecule-containing group.

3. The compound of claim 2, wherein the biomolecule is an antibody, a peptide, a protein, an amino acid, a nucleoside, a nucleotide, a nucleic acid, an oligonucleotide, a carbohydrate, a lipid, a hapten, or a receptor ligand.

4. The compound of claim 1, wherein R³ is

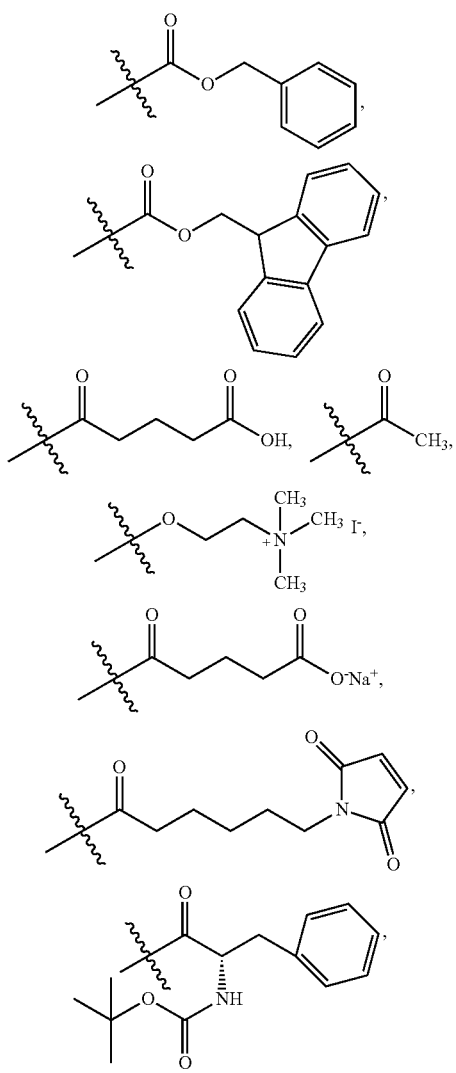

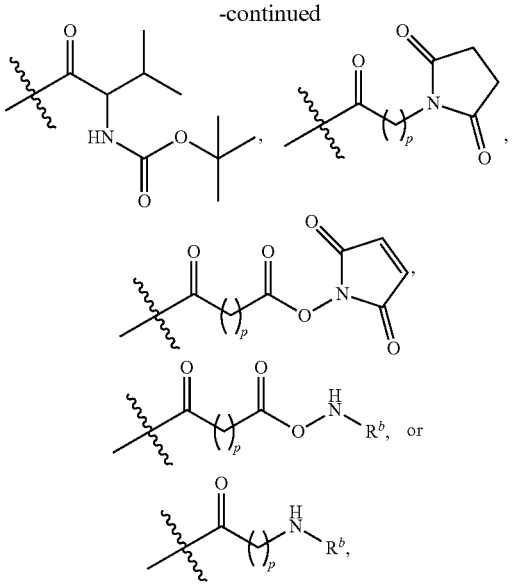

where p is 1, 2, 3, 4, or 5, and $R^b$ is a biomolecule.

5. The compound of claim 4, wherein $R^b$ is an antibody, a peptide, a protein, an amino acid, a nucleic acid, nucleotide, an oligonucleotide, a lipid, a hapten, or a receptor ligand.

6. The compound of claim 1, wherein each $R^a$ independently is hydrogen or halo, and m is 2 or 3.

7. The compound of claim 1, wherein R¹⁴ to R¹⁷ are methyl.

8. The compound of claim 1, wherein n is 2.

9. The compound of claim 1, wherein:
R⁵, R⁶, R⁸, R¹⁰, R¹¹ and R¹³ are hydrogen;
R⁴ and R⁹ independently are lower alkyl or a sulfonate-containing group; and
R⁷ and R¹² independently are hydrogen, a sulfonate-containing group, or a trialkyl amino group.

10. The compound of claim 9, wherein:
R⁴ and R⁹ are n-propyl or —(CH₂)₄SO₃⁻; and
R⁷ and R¹² are hydrogen or —SO₃⁻Na⁺.

11. The compound of claim 1, having the general formula:

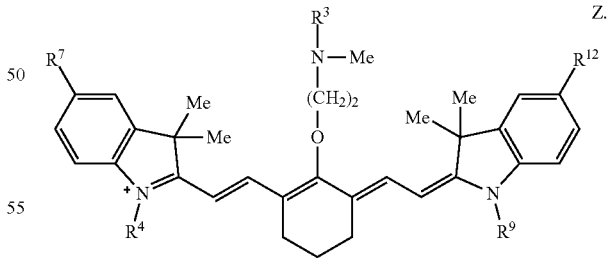

12. The compound of claim 1, wherein:
n is 2;
R¹ is —CH₂—;
m is 2;
R² is methyl;
R¹⁴ to R¹⁷ are methyl;
R⁵, R⁶-R⁸ and R¹¹-R¹³ are hydrogen;
R⁴ and R⁹ are n-propyl;
Z is halide, and $R^3$ is

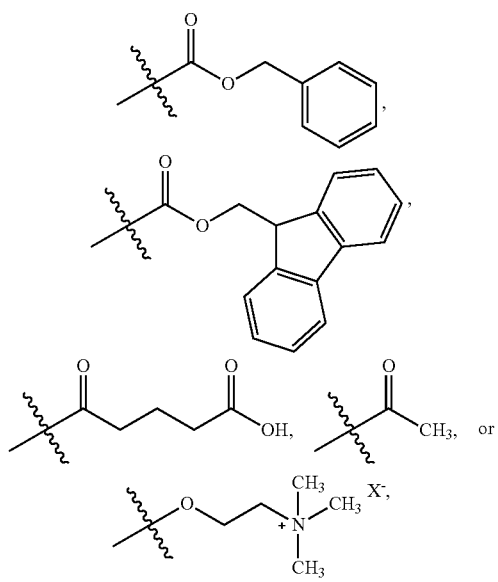

where $X^-$ is a halide.

13. The compound of claim 1, wherein:
n is 2;
$R^1$ is —$CH_2$—;
m is 2;
$R^2$ is methyl;
$R^{14}$ to $R^{17}$ are methyl;
$R^5$, $R^6$, $R^8$, $R^{10}$, $R^{11}$ and $R^{13}$ are hydrogen;
$R^4$ and $R^9$ are —$(CH_2)_4SO_3^-$;
$R^7$ and $R^{12}$ are —$SO_3^-$;
Z is an alkali metal cation, and
$R^3$ is

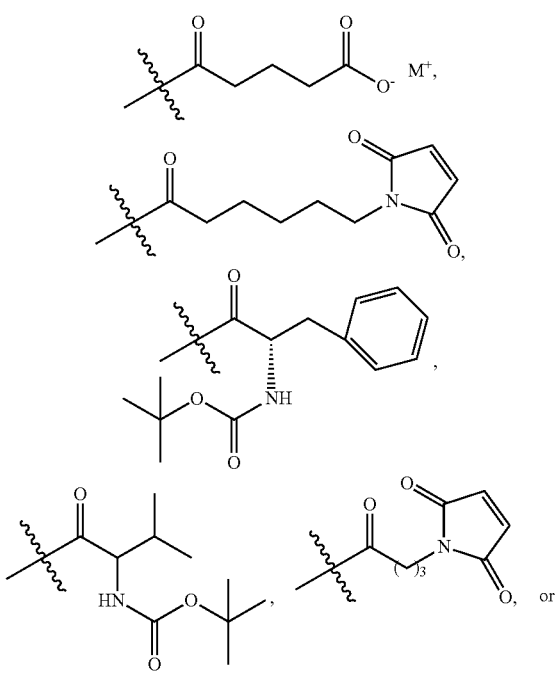

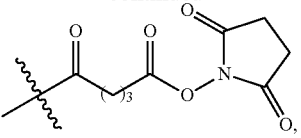

where $M^+$ is a proton or an alkali metal cation.

14. A method, comprising:
contacting a biological sample with a compound of claim 1;
irradiating the biological sample by application of light having a wavelength or range of wavelengths in the near-infrared range; and
detecting fluorescence of the irradiated biological sample, wherein fluorescence indicates presence of the compound in the biological sample.

15. The method of claim 14, wherein detecting fluorescence comprises obtaining a fluorescence-based image of the irradiated biological sample.

16. The method of claim 15, wherein the compound comprises a biomolecule capable of binding to a target suspected of being present within the biological sample and fluorescence indicates the target is present in the biological sample, the method further comprising:
removing unbound compound from the biological sample prior to obtaining the image.

17. The method of claim 14, wherein the biological sample comprises cells in solution and the compound comprises a moiety capable of binding to at least some cells in the solution, the method further comprising performing flow cytometry to separate cells to which the compound has bound from cells to which the compound did not bind.

18. The method of claim 14, wherein contacting the biological sample with the compound is performed in vivo by administering the compound to a subject.

19. The method of claim 18, wherein the compound comprises a biomolecule capable of binding to a target suspected of being present within the biological sample.

20. The method of claim 19, wherein the target is an antigen, and the compound comprises an antibody capable of recognizing and binding to the antigen.

21. The method of claim 19, wherein:
irradiating the biological sample comprises irradiating a target area of the subject with near-infrared radiation; and
detecting fluorescence comprises obtaining an image of the irradiated target area, wherein fluorescence in the image indicates presence of the target in the target area.

22. The method of claim 19, wherein the target is a tumor and the target area is an area in which the tumor is located.

23. The method of claim 22, wherein the biomolecule is capable of recognizing and binding to cells of the tumor, irradiating the biological sample comprises irradiating the target area of the subject with near-infrared radiation, and detecting fluorescence indicates presence of tumor cells in the target area, the method further comprising:
excising fluorescent tumor cells from the target area.

24. The method of claim 18, wherein the compound comprises a drug, the biological sample is a bodily fluid or tissue, and detecting fluorescence of the irradiated biological sample indicates presence of the drug in the biological sample.

25. The method of claim 18, wherein detecting fluorescence of the biological sample is performed ex vivo.

* * * * *